(12) United States Patent  
Bobo, Jr.

(10) Patent No.: US 7,776,025 B2
(45) Date of Patent: Aug. 17, 2010

(54) METHOD FOR PROVIDING MEDICAMENT TO TISSUE

(75) Inventor: Donald E. Bobo, Jr., Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 548 days.

(21) Appl. No.: 10/021,132

(22) Filed: Oct. 29, 2001

(65) Prior Publication Data

US 2003/0083607 A1 May 1, 2003

(51) Int. Cl.
*A61M 25/00* (2006.01)
*A61M 29/00* (2006.01)
*A61M 31/00* (2006.01)

(52) U.S. Cl. .................... 604/509; 604/96.01; 604/523

(58) Field of Classification Search ................. 604/20, 604/96.01, 96.05, 507–509, 523, 528, 529; 600/3, 7, 10–17
See application file for complete search history.

(56) References Cited

U.S. PATENT DOCUMENTS

| 4,445,892 | A | | 5/1984 | Hussein et al. |
| 5,304,173 | A | * | 4/1994 | Kittrell et al. ................. 606/15 |
| 5,725,523 | A | * | 3/1998 | Mueller ....................... 606/15 |
| 5,807,388 | A | * | 9/1998 | Jeevanandam et al. ........ 606/15 |
| 5,925,012 | A | * | 7/1999 | Murphy-Chutorian et al. ... 604/20 |
| 5,968,059 | A | | 10/1999 | Ellis et al. |
| 6,019,756 | A | | 2/2000 | Mueller et al. |
| 6,067,988 | A | * | 5/2000 | Mueller ....................... 604/15 |
| 6,079,414 | A | | 6/2000 | Roth |
| 6,086,582 | A | | 7/2000 | Altman et al. ................ 606/41 |
| 6,143,019 | A | | 11/2000 | Motamedi et al. |
| 6,161,543 | A | * | 12/2000 | Cox et al. ..................... 606/47 |
| 6,165,188 | A | | 12/2000 | Saadat et al. |
| 6,283,951 | B1 | * | 9/2001 | Flaherty et al. ............. 604/529 |
| 6,565,528 | B1 | * | 5/2003 | Mueller ...................... 606/198 |
| 6,565,555 | B1 | * | 5/2003 | Ryan et al. .................... 606/18 |
| 6,645,199 | B1 | * | 11/2003 | Jenkins et al. ................ 606/41 |
| 6,805,860 | B1 | * | 10/2004 | Alt .............................. 604/509 |
| 2001/0007937 | A1 | | 7/2001 | MacKin |
| 2001/0049497 | A1 | * | 12/2001 | Kalloo et al. ............ 604/96.01 |

FOREIGN PATENT DOCUMENTS

| EP | 0 934 728 A2 | 8/1999 |
| WO | WO 99/39624 | 8/1999 |
| WO | WO 01/39682 A1 | 6/2001 |

* cited by examiner

*Primary Examiner*—David Shay
(74) *Attorney, Agent, or Firm*—Guy L. Cumberbatch, Esq.

(57) ABSTRACT

A system for delivering medicaments to tissue including a delivery member and an optical fiber formed together into a unitary structure. The optical fiber has an inlet attached to a laser energy source and an outlet for emitting laser energy. The delivery member has an inlet attached to a medicament source and an outlet for injecting medicament. A handpiece is adapted to receive the ablating and injecting device in a controlled and movable relationship and may include at least one tissue stabilizing member thereon. In use, the distal end of the handpiece is placed against tissue to be ablated. The optical fiber is advanced into the tissue while emitting laser energy thereby ablating the tissue and forming a channel therein. During retraction, medicament may be injected into the channel or into the tissue surrounding the channel.

6 Claims, 24 Drawing Sheets

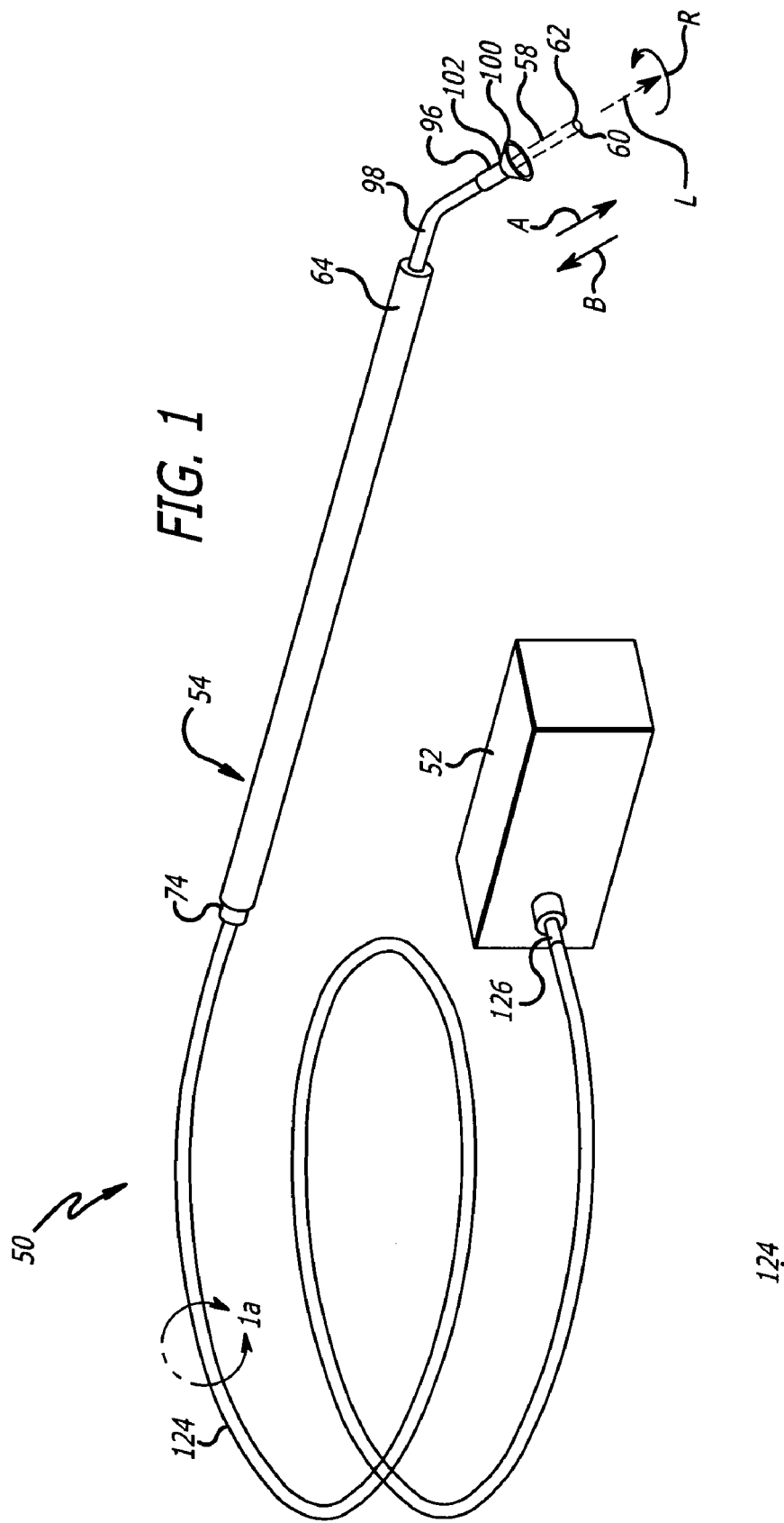

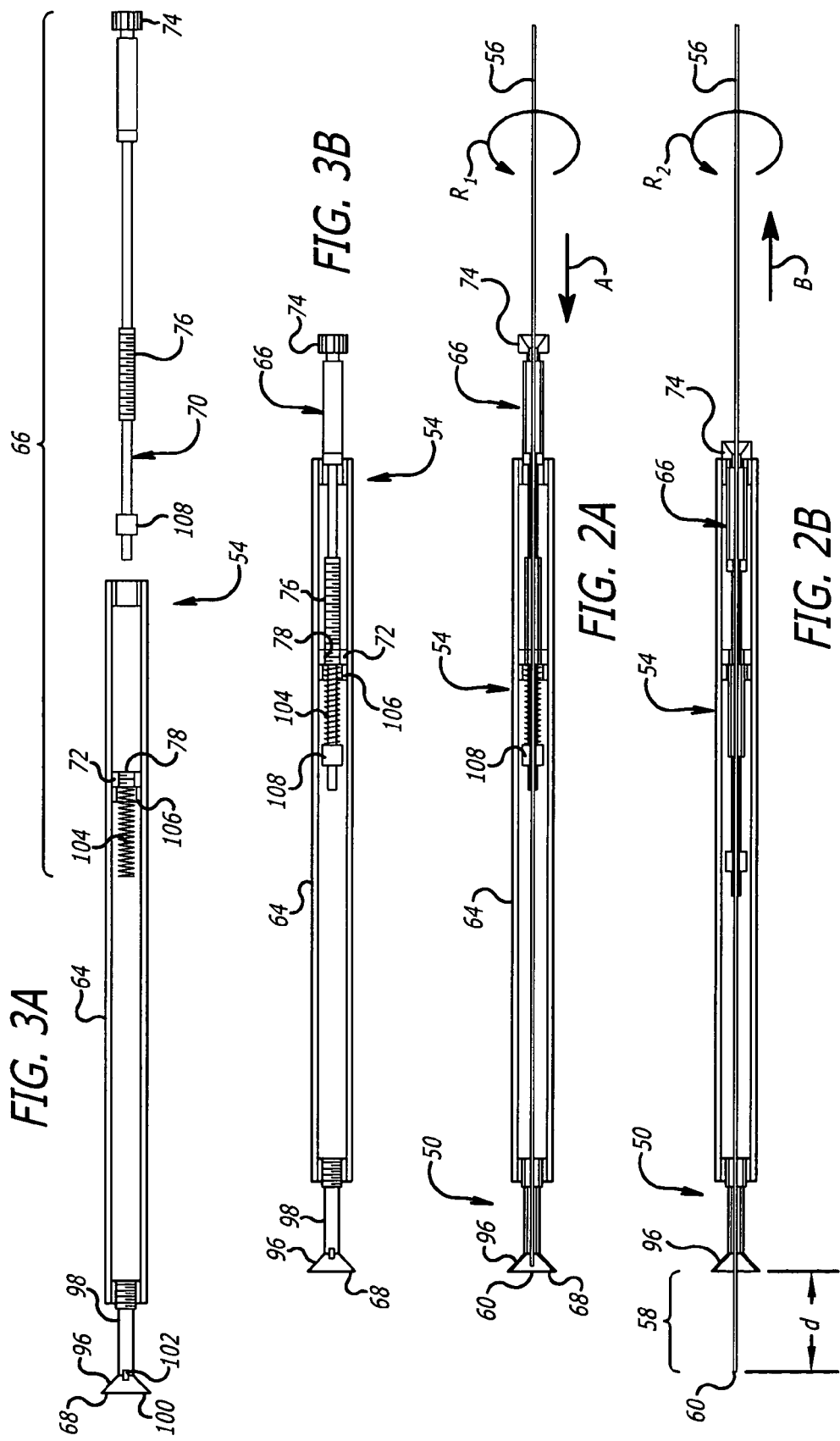

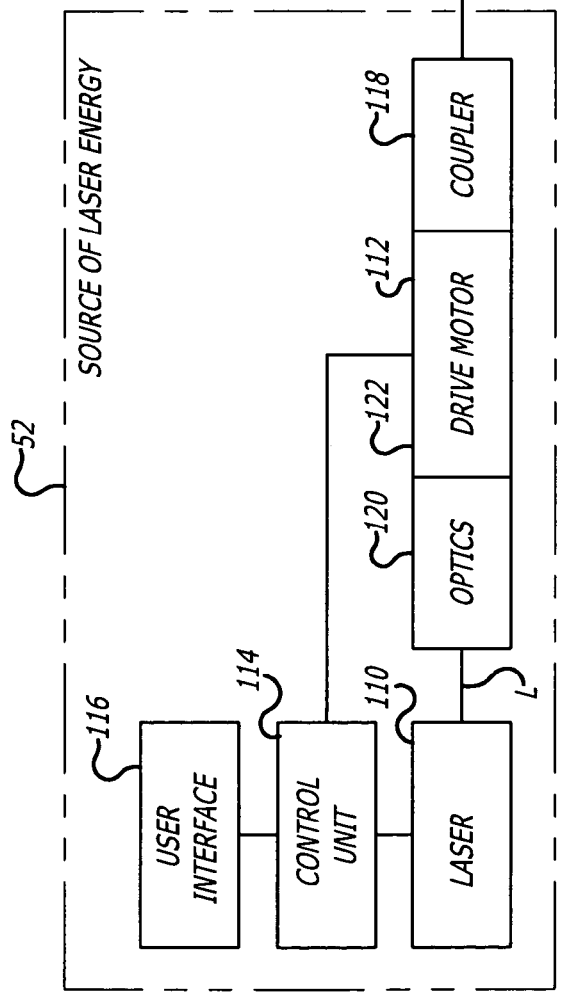
FIG. 9
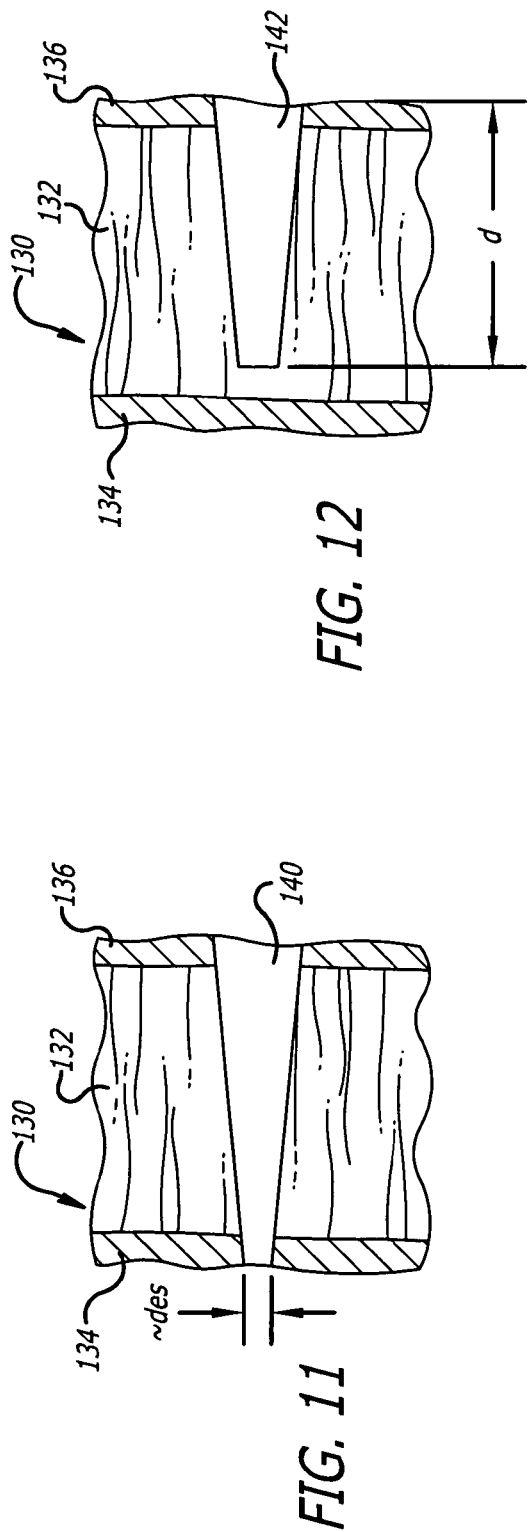
FIG. 12
FIG. 11

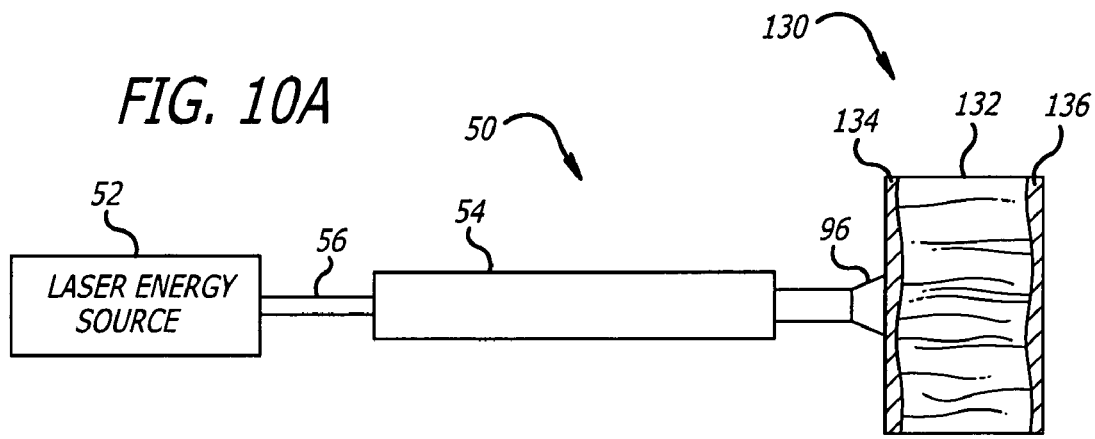
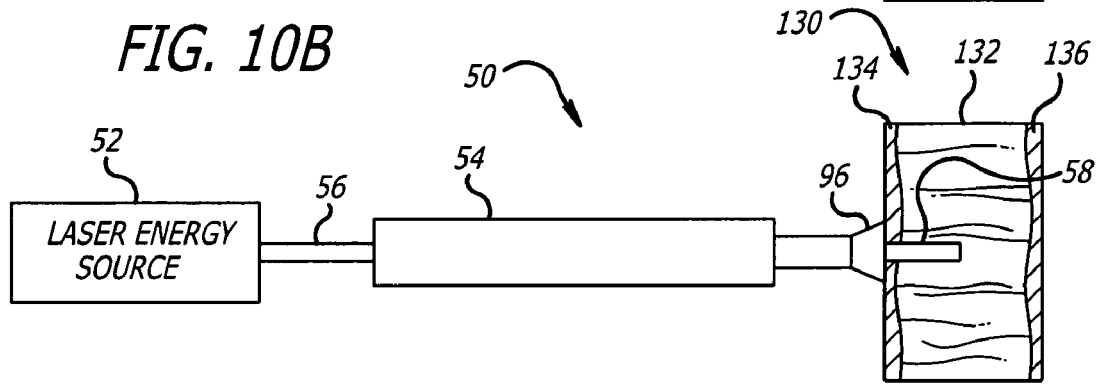
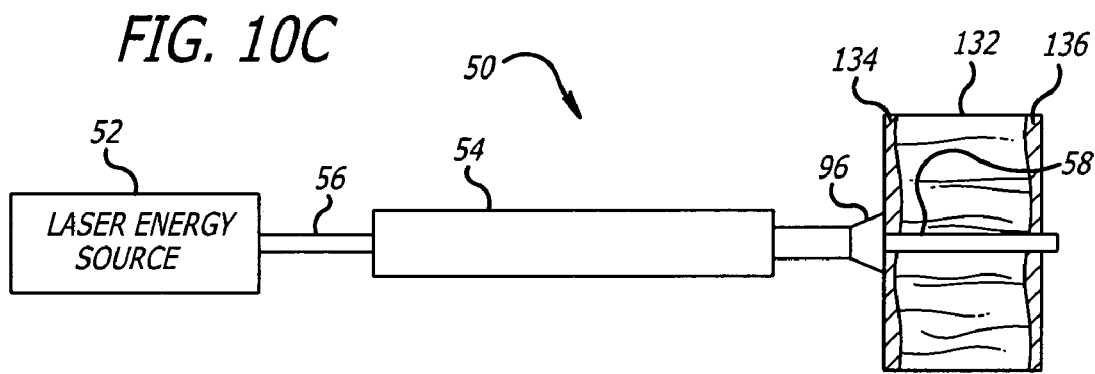
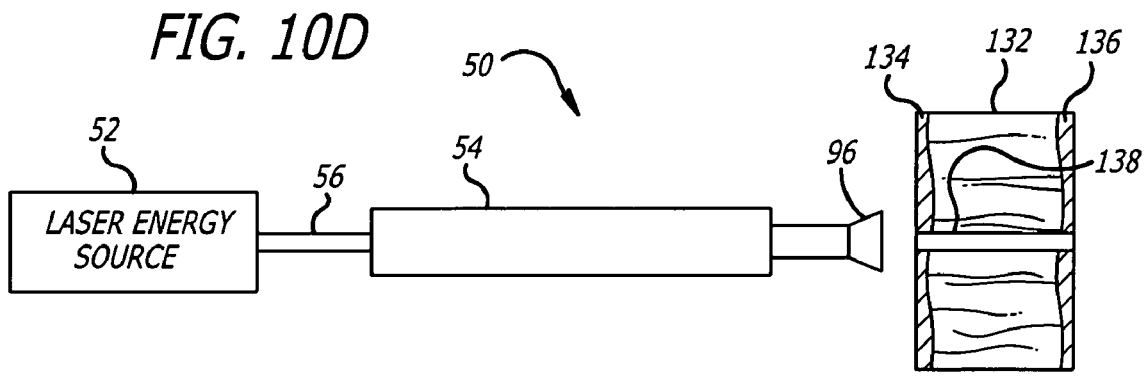

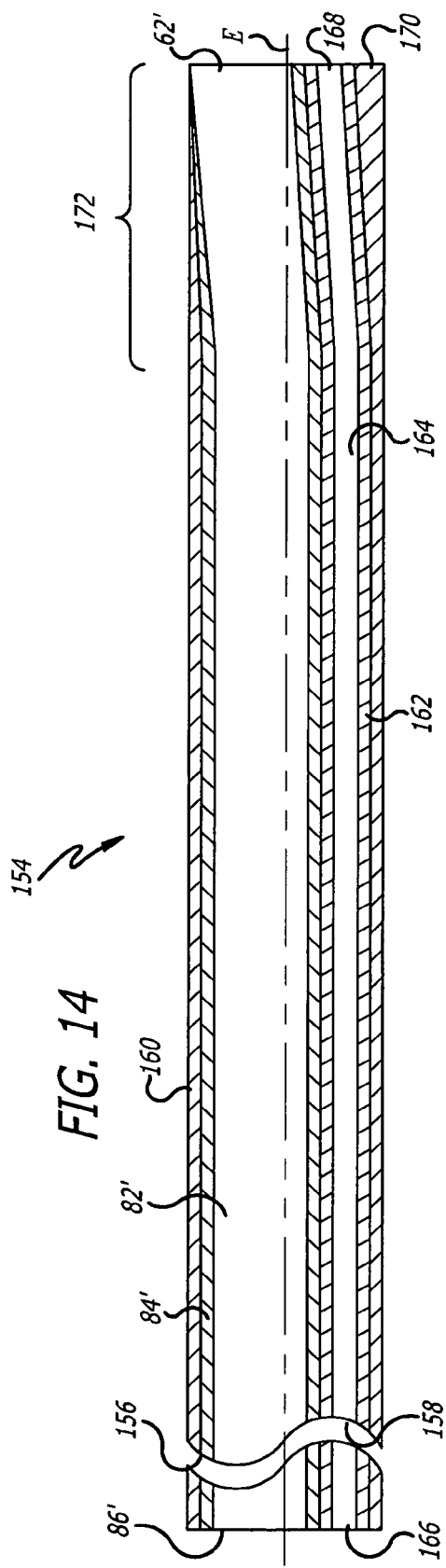
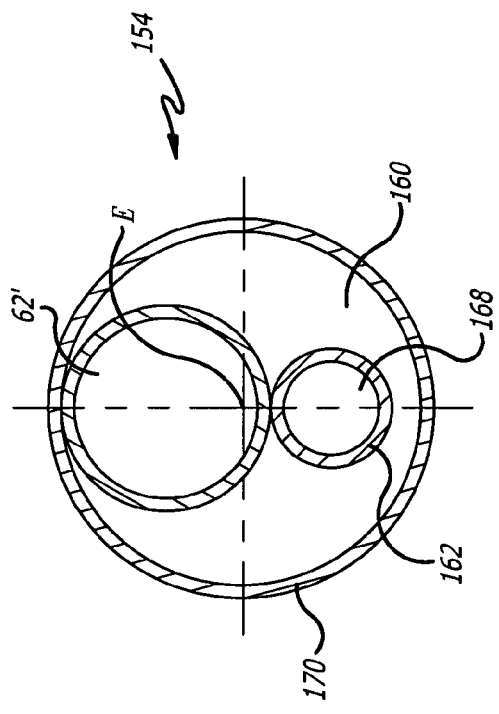

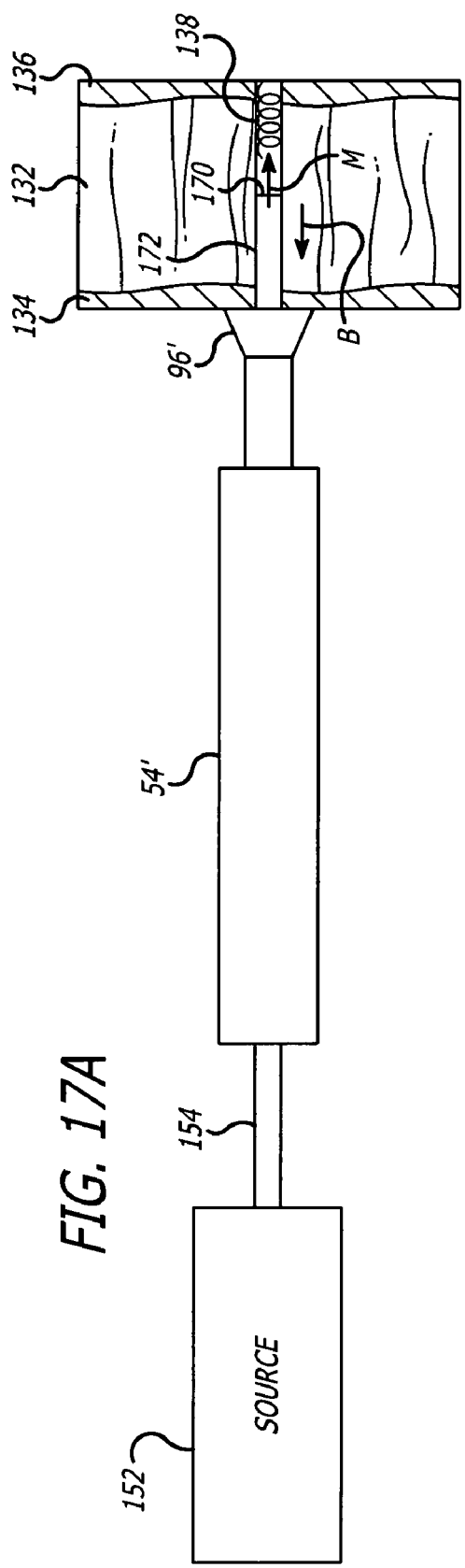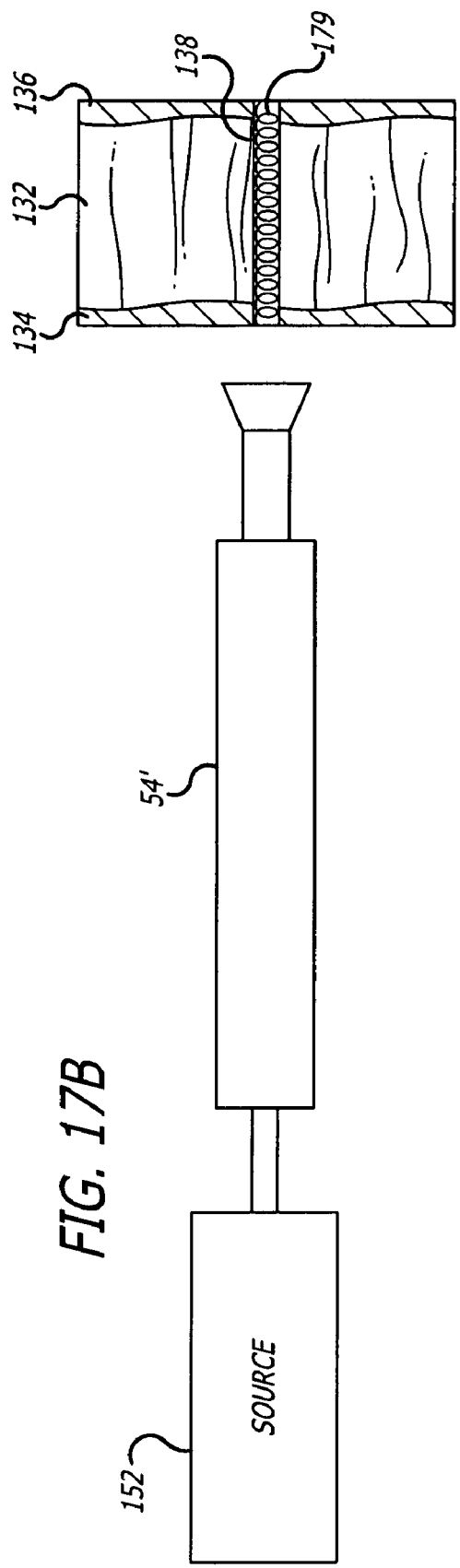

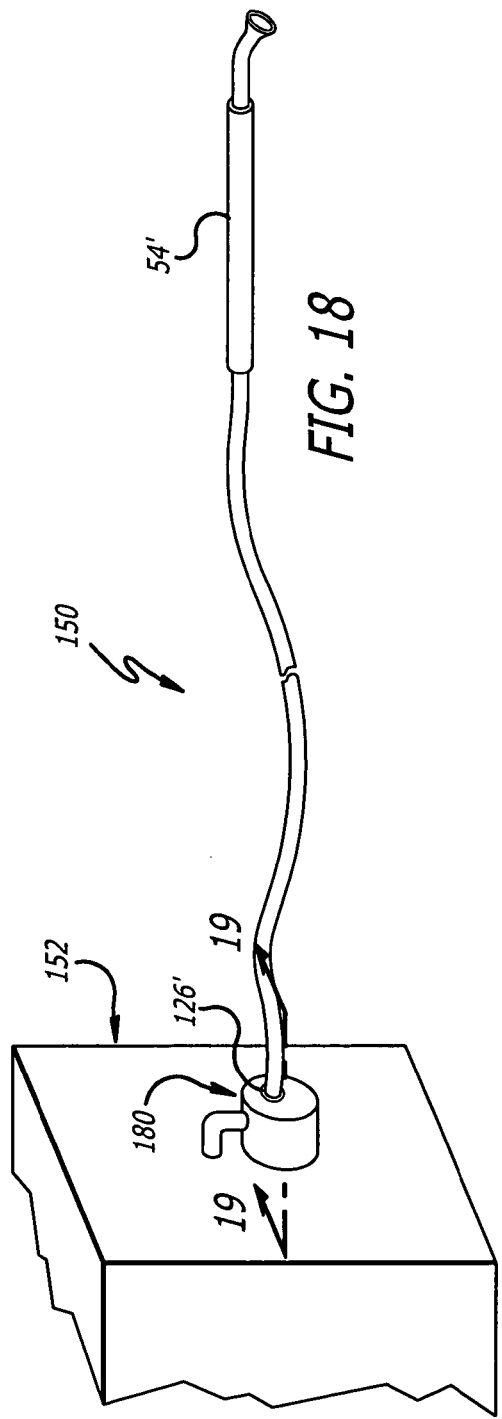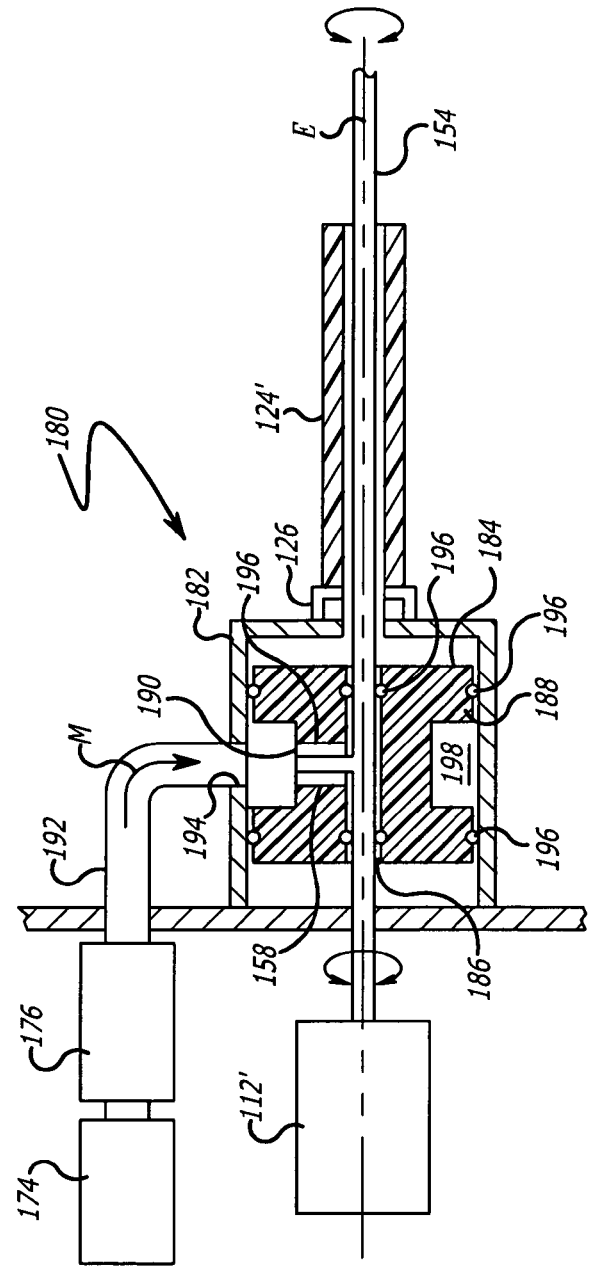
FIG. 18
FIG. 19

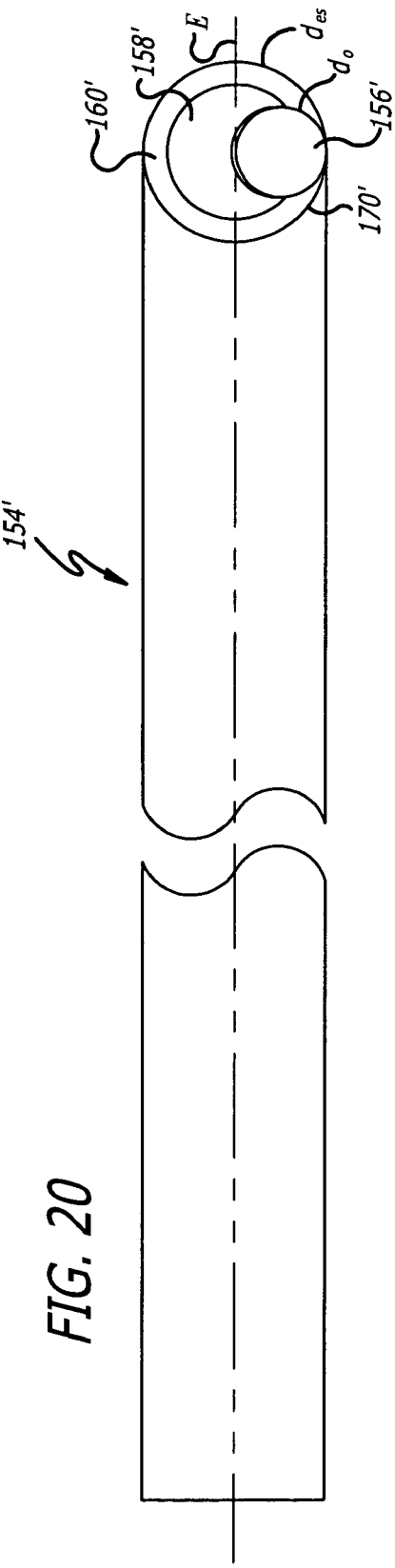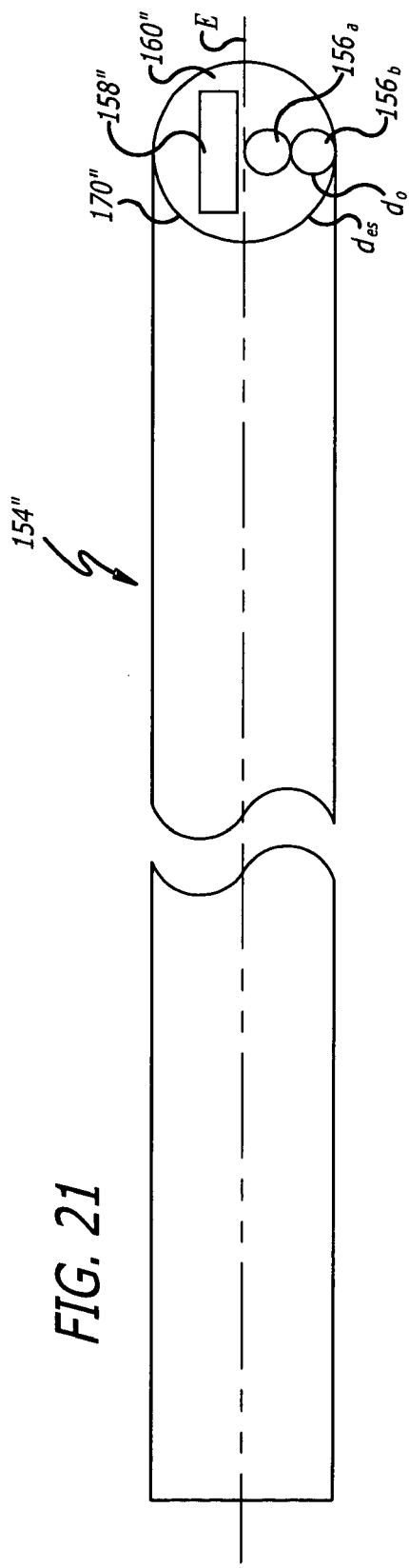
FIG. 20
FIG. 21

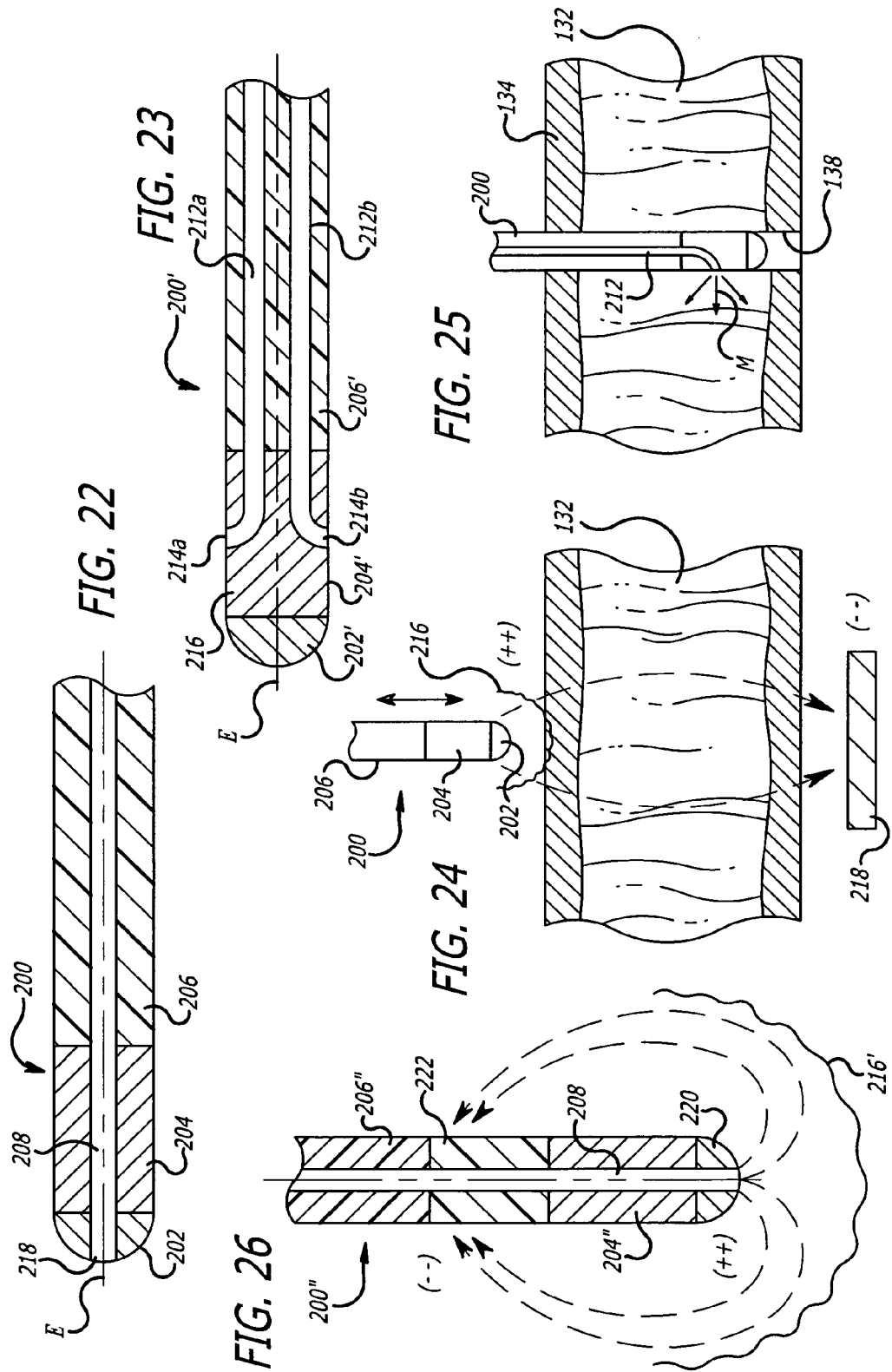

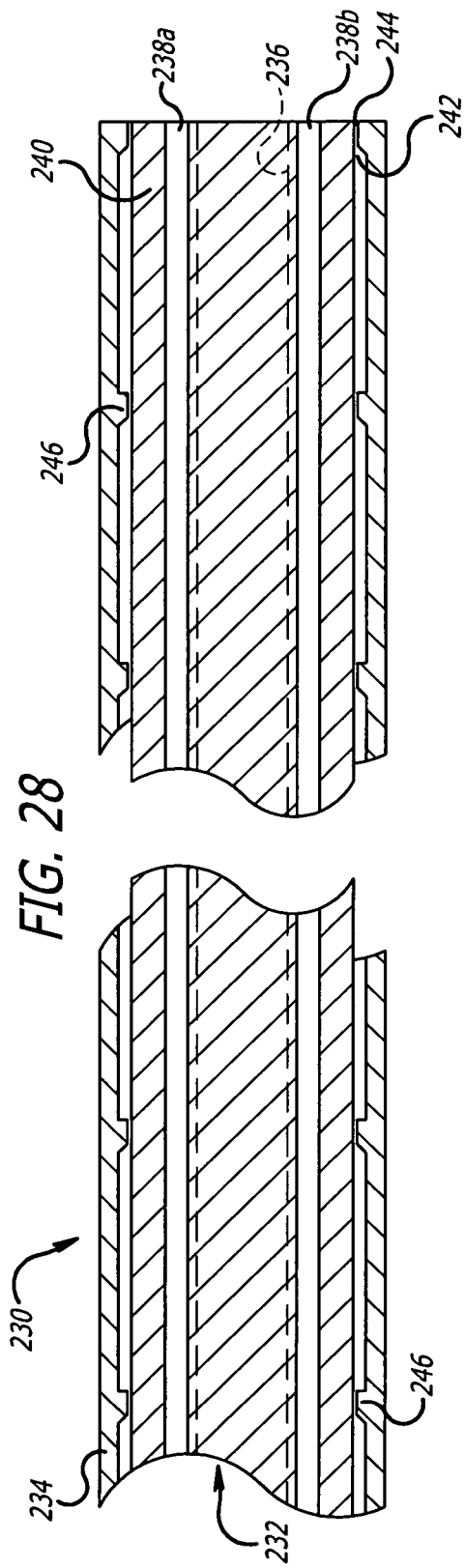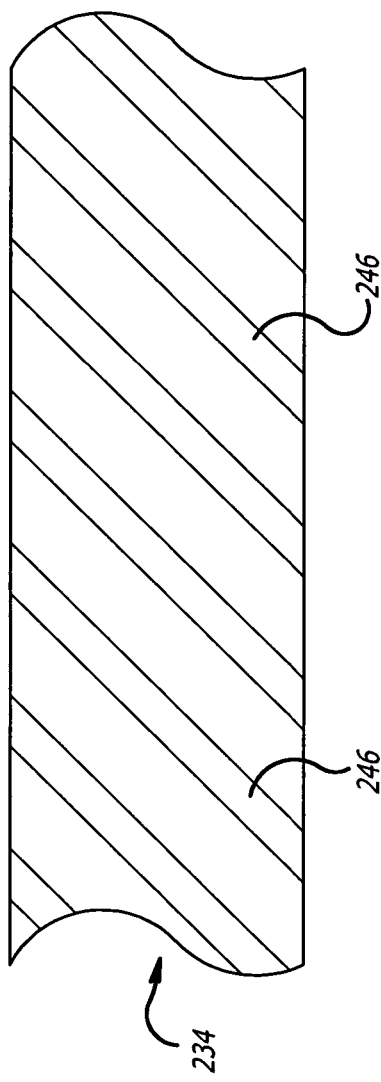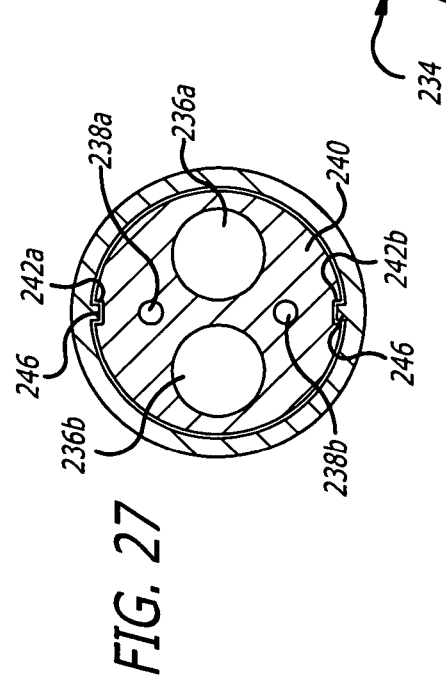

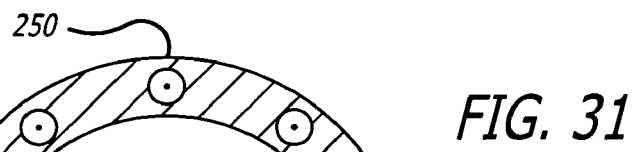
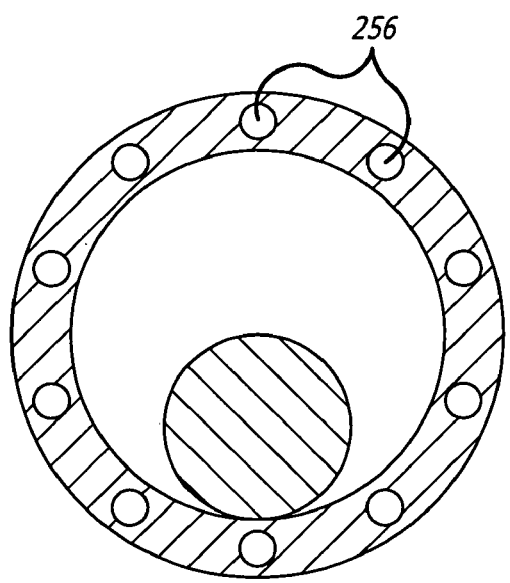
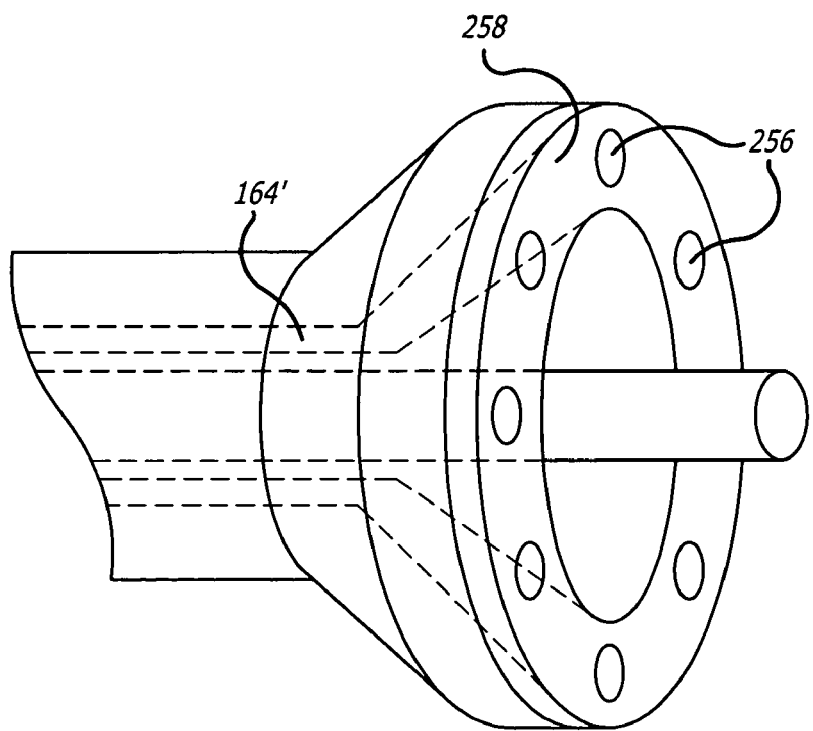

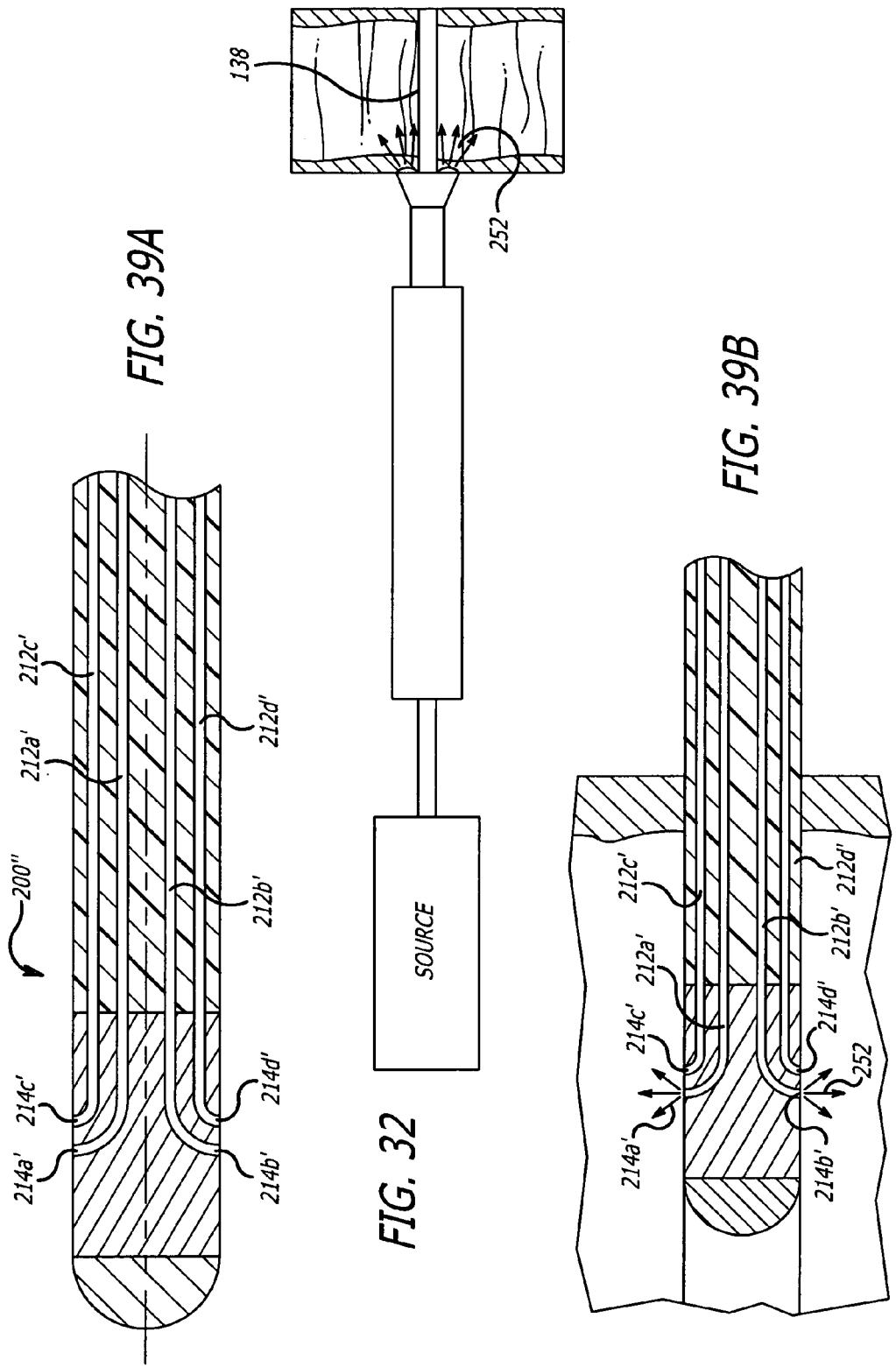

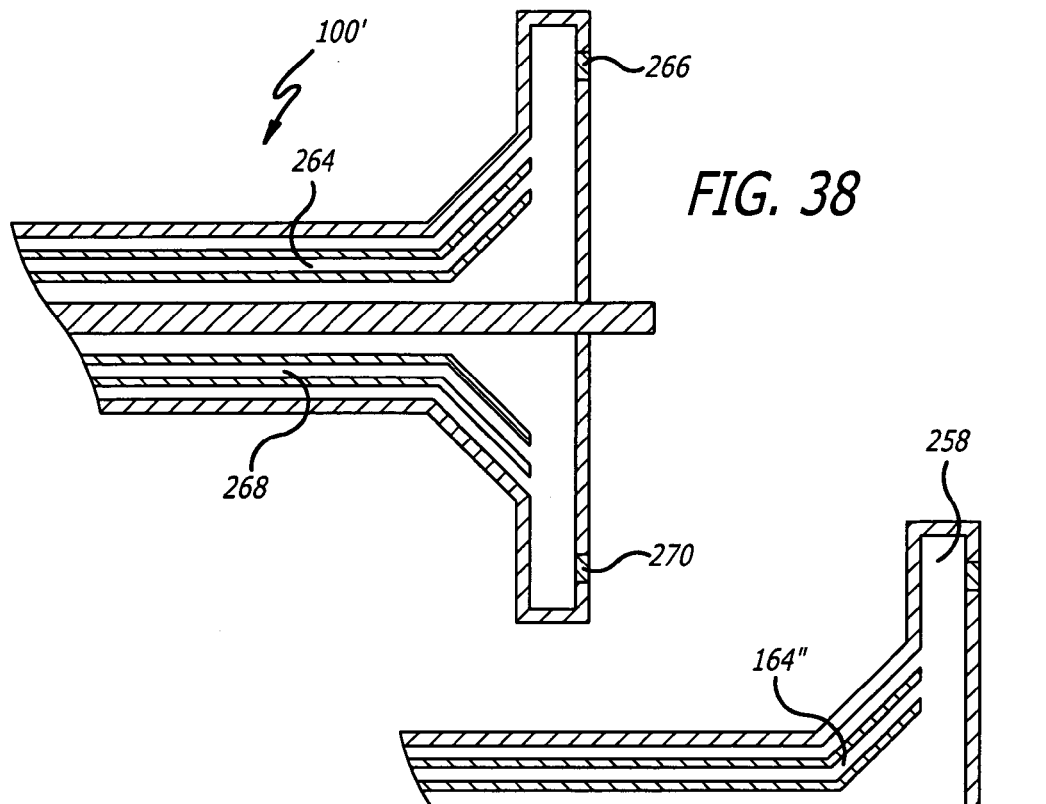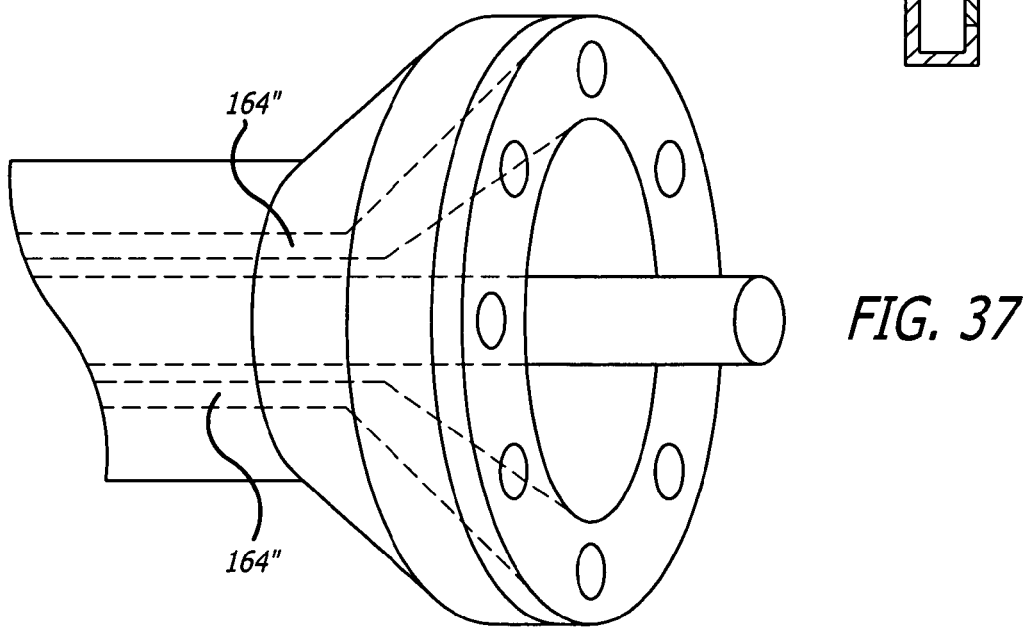

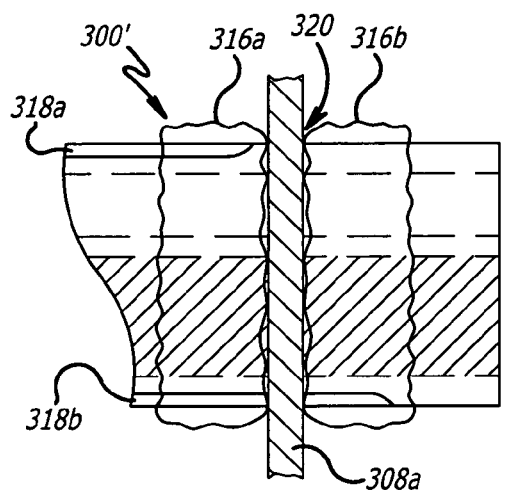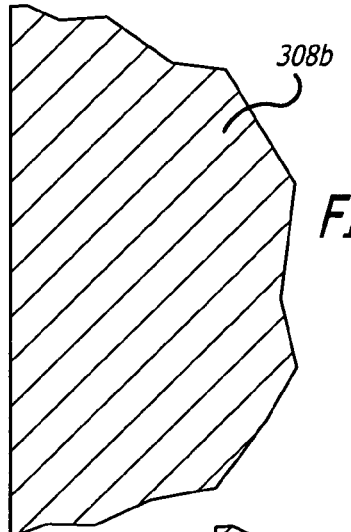
FIG. 42a
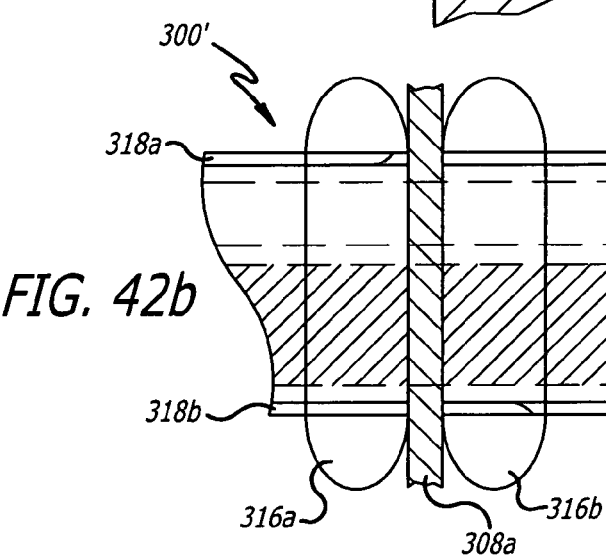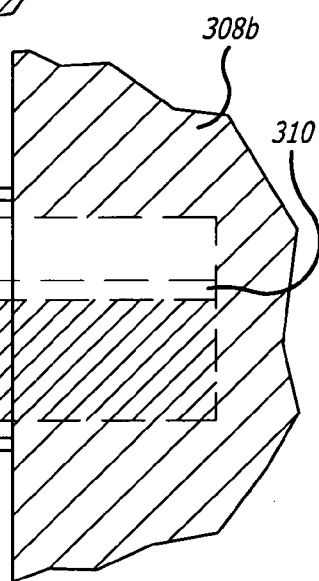
FIG. 42b
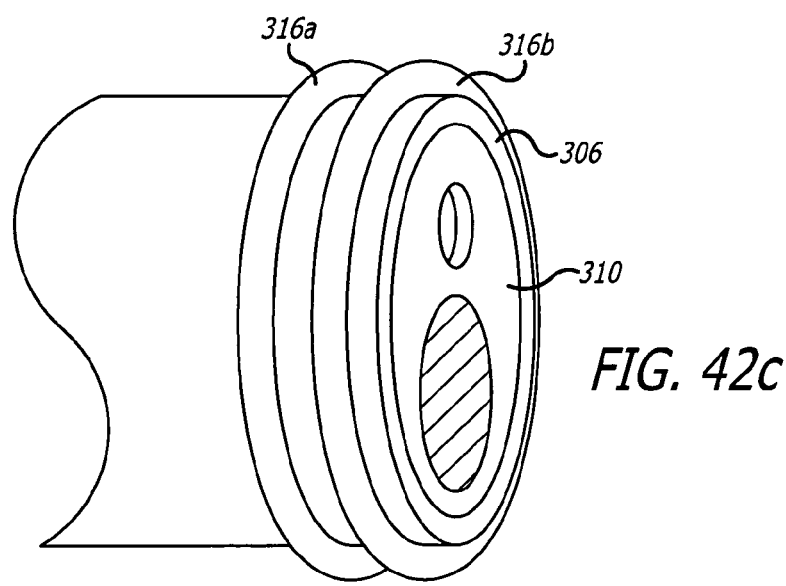
FIG. 42c

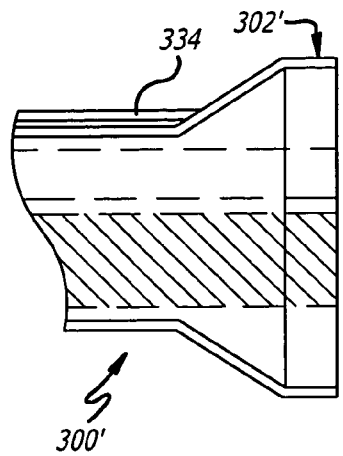
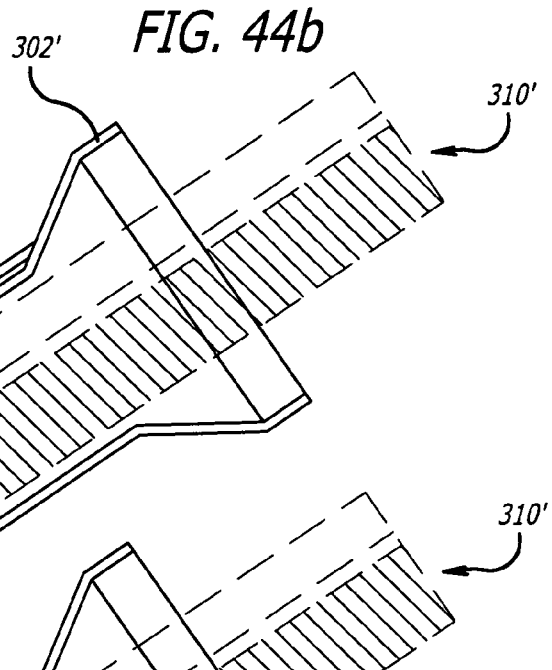
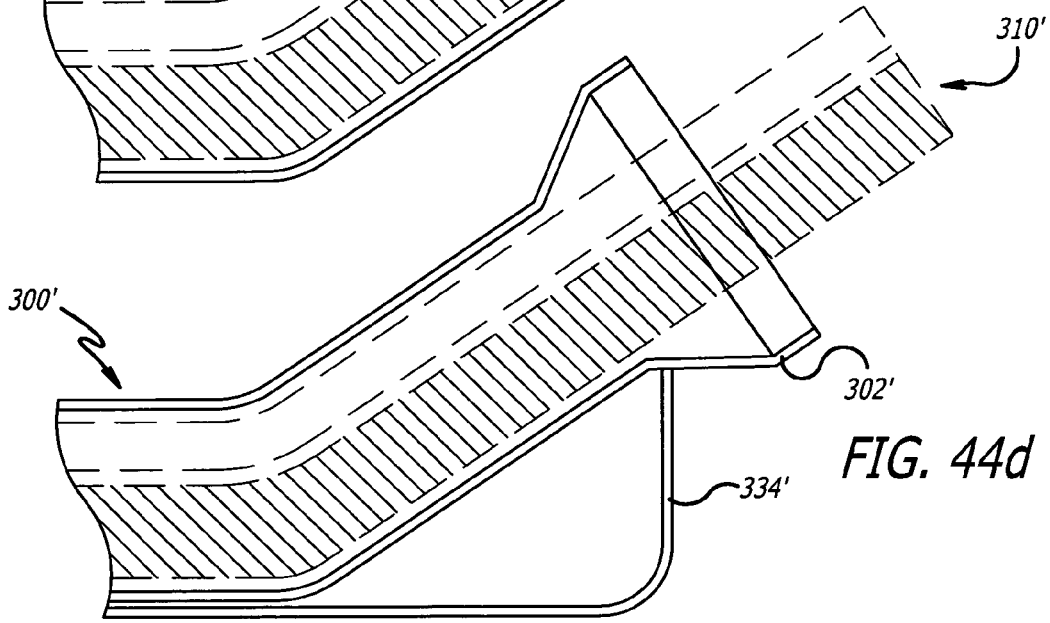
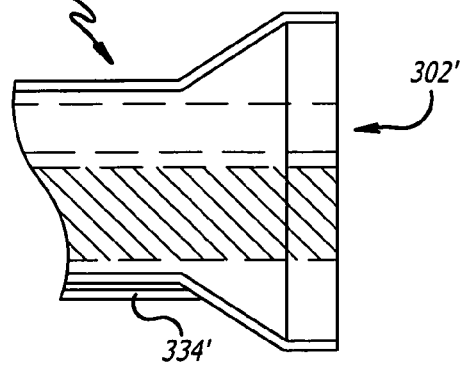

METHOD FOR PROVIDING MEDICAMENT TO TISSUE

CROSS REFERENCE TO RELATED APPLICATIONS

This application discloses subject matter related to our co-pending U.S. Continuation-In-Part patent application Ser. No. 09/452,776, filed Dec. 2, 1999, which claims priority from U.S. patent application Ser. No. 09/108,553 Jul. 1, 1998, all naming Donald E. Bobo, Jr. as first inventor. The disclosures of the aforementioned U.S. patent applications, "the above applications" are hereby incorporated herein by reference thereto.

BACKGROUND OF THE INVENTION

Heart disease is a significant health condition affecting millions of people worldwide. Cardiomyopathy (cardio meaning "heart" and myopathy meaning "muscle disease") refers generally to a group of disorders that directly affect the muscle of the heart walls, or myocardium. As a result, all the chambers of the heart are negatively affected and the ability of the heart to function as a pump is disrupted, thereby resulting in inadequate or inconsistent blood flow to the various organs or tissues of the body.

Generally, one of three types on non-ischemic heart disease, that is, heart tissue damage not caused by heart attack, may be present in a patient: dilated congestive, hypertrophic, or restrictive. Dilated congestive cardiomyopathy damages the fibers of the heart muscle and weakens the walls of the heart's chambers, resulting in the chambers losing some capacity to forcibly contract and pump blood through the circulatory system. Thereafter the chambers of the heart enlarge or dilate to compensate for the decrease pumping efficiency. The enlargement of the chamber may result in heart failure. Hypertrophic cardiomyopathy is characterized by a disorderly growth of heart muscle fibers resulting in the walls of the heart chambers becoming thick and bulky. Wall thickening is most pronounced in the walls of the left ventricle, the heart chamber which pumps blood to through the aorta to vital organs and tissues of the body. The thickening walls result in the trapping of blood within the heart during contraction, thereby providing an inadequate blood supply to the brain or other vital organs. Restrictive cardiomyopathy causes abnormal cells, proteins, or scar tissue to infiltrate the muscles and structures of the heart, causing the chambers to become stiff and bulky, thereby restricting blood flow to the heart.

Massive or multiple heart attacks may also lead to severe heart damage as a result of a disruption of the blood supply to the heart muscle. The heart damage resulting from heart attacks may include functional impairment and structural abnormalities similar to those found in other types of cardiomyopathy. This type of heart disease, resulting from coronary artery disease, is called ischemic cardiomyopathy (ischemic meaning "lacking oxygen").

Patients with ischemic cardiomyopathy may initially be treated with medication to relieve heart failure symptoms and to improve blood flow through the diseased arteries. These medications may include nitroglycerin, calcium channels blockers, and angiotensin—converting enzymes (ACE) inhibitors. When symptoms of heart failure and coronary artery disease cannot be controlled with medications coronary angioplasty or surgery may be considered. Some patients, due to the advanced state of heart disease, may become too ill to survive conventional coronary surgery. Non-surgical procedures such as percutaneous transluminal coronary angioplasty, laser angioplasty, and atherectomy have been developed. One alternative to the aforementioned procedures is known as Transmyocardial Revascularization (TMR). In such procedures, channels are formed in the ventricle wall of the heart. These channels provide blood flow to ischemic heart muscle.

Pioneering methods for performing TMR involved the use of needles for physically puncturing holes in the heart wall. These methods resulted in only a temporary delivery of blood to the myocardium because the holes quickly healed at the endocardium, preventing oxygenated blood from entering the myocardium. One of the more recent and exciting methods of performing TMR is through the use of lasers. It has been observed that new holes or channels formed in the heart wall by a laser tend to heal at the epicardium, which prevents blood loss, and promote blood perfusion into the ischemic region of the myocardium.

Lasers have proven to be a widely useful and applicable tool in modern medical techniques, particularly in minimally invasive surgical procedures. A laser is able to produce high-intensity and high-energy light at a single frequency. The energy of laser light is measured in joules (J), or waft-seconds (W-s), and the power of a laser is measured in wafts (W).

One of the conventional surgical apparatus for performing TMR consists of a laser and an optical fiber. A surgeon places the end of the optical fiber against the epicardium to ensure that all the laser light is focused at the desired point, and then the laser is fired. In order to form the new channel completely through the heart wall and into the chamber, the surgeon needs to tactilely urge the optical fiber into and through the epicardium, the myocardium, and the endocardium. Because of the nature of ischemic cardiomyopathy, the thickness of the diseased myocardium is irregular and greater than normal. Accordingly, the surgeon needs to tactilely urge the optical fiber through the heart wall at each location.

Execution of TMR procedure takes a certain amount of time to accomplish safely and involves a certain amount of guesswork on the part of the surgeon. This procedure is complicated by the beating of the heart. Accordingly, the firing of the laser needs to be synchronized with the beating of the heart and the device should be maintain its position with respect to the epicardium. In addition, irregularly shaped holes may result if the surgeon does not urge the optical fiber into the tissue at a constant rate or if the handpiece disengages the epicardium. For example, a cavity within the new hole may be formed if the surgeon slowed down or paused briefly at a particular location because more tissue at that location would be ablated by the increase in laser energy emitted over time. In addition, the increase in emitted laser energy may cause excessive trauma to the surrounding tissue at that location.

With a channel formed, the surgeon may treat the area with a medicament. For example, an angiogenic material may be deposited or injected into the channel or surrounding tissue. As such, the ability to isolate the channel or surrounding area is preferred, thereby preventing medicament "washout". Currently, methods of preventing medicament washout have generally proven to be unsuccessful.

Thus, there is a need for a system of delivery system capable of stabilizing tissue, forming a channel within the tissue, and delivering medicament to the channel or the surrounding area. It is further desirable to have a system capable of isolating an area of interest prior to delivering medicament thereto, thereby preventing medicament washout.

BRIEF SUMMARY OF THE INVENTION

These and other objects are achieved by the surgical apparatus and associated methods of the present invention which provide a medicament delivery system which stabilizes tissue, forms holes, pockets, or channels in tissue by removing or displacing tissue, and then delivers medicament to the hole, pocket, or channel or to the tissue surrounding the hole or channel. Tissue is preferably removed or displaced with laser ablation but may be removed or displaced by other methods, for example, with high-frequency electrical energy.

The system for delivering medicament to tissue in accordance with the present invention may be utilized to stabilize or isolate tissue, form a hole or channel in tissue, for example, cardiac tissue (myocardium), and then deliver medicament to the tissue. The medicament may include, for example, a therapeutic agent for the treatment of cardiovascular disease, a growth factor that promotes angiogenesis, a gene that encodes for said growth factor, or any other therapeutic agent or gene therapy agent that promotes angiogenesis. The medicament may be provided to the tissue by partially or fully filling the hole or channel with the medicament, or by injecting the tissue surrounding the hole or channel with the medicament. This process may be repeated a plurality of times to form and fill a plurality of holes and channels in a targeted area of tissue. In contrast with conventional systemic delivery approaches, the medicament-delivery system of the present invention delivers medicament in a controlled manner to a stabilized or isolated tissue.

The medicament-delivery system of the present invention may form pockets or channels in stabilized or isolated tissue by removing or displacing tissue with laser ablation. It has been found that tissue ablation with laser energy stimulates a natural biological process of angiogenesis in the heart. In addition, administering medicaments such as growth factors that promote angiogenesis have been found to promote angiogenesis in the heart. Accordingly, a synergistic stimulation and promotion of angiogenesis in the heart is created by augmenting the heart's natural angiogenic response to laser ablation with the delivery of growth factor to those areas of the myocardium which have been ablated. The coupling of the heart's natural response to the formation of channels with the delivery of growth factor into or adjacent to those pockets or channels provides a benefit to patients not heretofore possible.

In a broad aspect of the present invention, a system for delivering medicaments to tissue includes an tissue stabilizing ablation and injecting device and a handpiece. The ablating and injecting device includes an optical fiber and a delivery member formed together into a unitary structure with cladding. The optical fiber has an inlet for receiving laser energy from a laser energy source and an outlet for emitting laser energy. The delivery member has a lumen with an inlet for receiving medicament from a medicament source and an outlet for injecting medicament. The handpiece is adapted to receive the ablating and injecting device in a controlled and movable relationship. The distal end of the handpiece comprises at least one tissue stabilizing member, which engages the tissue and maintains the position of the handpiece in relation thereto. The tissue stabilizer may comprise, for example, deployable needles or barbs, vacuum stabilization devices, or balloons. In use, the handpiece is placed against the target tissue and the tissue stabilizing device is actuated. The ablating and injecting device is advanced beyond the distal end of the handpiece and into the tissue while emitting laser energy from the optical fiber. The emitted laser energy ablates the tissue as the optical fiber advances. The ablating and injecting device is then retracted from the tissue, thereby resulting in a channel formed in the tissue. While the device retracts, medicament is injected from the delivery member into the channel, thereby providing a plug within the channel. The medicament may include growth factor alone or in combination with a cellular matrix which enhances angiogenesis in the tissue.

In an alternate embodiment, a sealing device may be utilized to ensure the medicament remains in contact with the tissue channel or surrounding tissue. For example, a sealing balloon may be used to isolate the region and prevent medicament washout.

In another embodiment, the distal portion of the ablating and injecting member may be flexible and capable of steering or biasing by the operator.

Other aspects, features, and advantages of the present invention will become apparent to those persons having ordinary skill in the art to which the present invention pertains from the following description taken in conjunction with the accompanying drawings.

BRIEF DESCRIPTION OF THE DRAWINGS

FIG. 1 is a perspective view of an exemplary embodiment of a tissue drill of the present invention;

FIG. 1A is a cross-sectional view of an exemplary optical fiber of the invention taken along line 1A of FIG. 1;

FIG. 2A is a diagrammatic view of the exemplary tissue drill of the present invention, illustrating a handpiece receiving an optical fiber in a retracted position;

FIG. 2B is a diagrammatic view similar to that of FIG. 2A, illustrating the optical fiber in an advanced position;

FIG. 3A is a diagrammatic view of an exemplary handpiece of the tissue drill of the present invention, illustrating the handpiece disassembled;

FIG. 3B is a diagrammatic view similar to that of FIG. 3A, illustrating the handpiece assembled;

FIG. 9 is a schematic view of an exemplary source of laser energy of the present invention;

FIG. 10A is a schematic view of an exemplary tissue drill of the present invention, particularly illustrating a step of a preferred tissue-drilling procedure implementing the tissue drill;

FIG. 10B is a view similar to that of FIG. 10A, illustrating a subsequent step in the tissue-drilling procedure;

FIG. 10C is a view similar to that of FIG. 10B, illustrating another subsequent step in the tissue-drilling procedure;

FIG. 10D is a view similar to that of FIG. 10C, illustrating yet another subsequent step in the tissue-drilling procedure;

FIG. 11 is a schematic view of tissue in which a hole has been drilled according to an exemplary method of the invention;

FIG. 12 is a schematic view of tissue in which a hole has been drilled according to another exemplary method of the invention;

FIG. 14 is a schematic cross-sectional view of an exemplary ablating and injecting device for use in the medicament delivery system of the present invention;

FIG. 15 is a schematic view of an end surface of the ablating and injecting illustrated in FIG. 14;

FIG. 17A is a schematic view of an exemplary medicament delivery system of the present invention, particularly illustrating a step of a preferred medicament-delivery procedure of the invention;

FIG. 17B is a view similar to that of FIG. 17A, illustrating a subsequent step in the medicament-delivery procedure;

FIG. 18 is a perspective view of a tissue-removal and medicament-delivery system in accordance with the invention, particularly illustrating a coupling assembly of the invention;

FIG. 19 is a cross-sectional view of an exemplary coupling assembly taken along line 19-19 of FIG. 18, with medicament injection and supply units shown schematically;

FIG. 20 is a diagrammatic view of an alternative embodiment of an exemplary ablating and injecting device for use in the medicament delivery system of the present invention;

FIG. 21 is a diagrammatic view of another embodiment of an exemplary ablating and injecting device for use in the medicament delivery system of the present invention;

FIG. 22 is a cross-sectional view of a tissue-removal and medicament-delivery device of the present invention, particularly configured to remove or displace tissue with high-frequency electrical energy;

FIG. 23 is a cross-sectional view of an alternative embodiment of a tissue-removal and medicament-delivery device of the present invention;

FIG. 24 is a schematic view of a step of a tissue-removing procedure incorporating the device of FIG. 22 or 23, particularly removing tissue with high-frequency electrical energy according to the invention;

FIG. 25 is a schematic view of a medicament-delivery step of the invention, particularly illustrating the delivery of medicament to tissue surrounding a hole or channel formed in tissue;

FIG. 26 is a cross-sectional view of another embodiment of an electrical-energy tissue-removal and medicament-delivery device in accordance with the invention;

FIG. 27 is a schematic view of another embodiment of a medicament-delivery system of the invention, particularly illustrating an ablating and injecting device received within a catheter with rifling;

FIG. 28 is a cross-sectional view of the medicament-delivery system of FIG. 27;

FIG. 29 is a developmental view of an exemplary catheter with rifling for use in the medicament-delivery system of FIG. 27;

FIG. 31 is a schematic view of the end surface of the head portion of FIG. 30;

FIG. 32 is a schematic view of the embodiment of FIG. 30, particularly illustrating a step of a preferred medicament-delivery procedure of the invention;

FIG. 34 is an end view of yet another exemplary embodiment of the head portion of the handpiece, illustrating ports around the perimeter of the head portion of the handpiece;

FIG. 35 is a perspective view of an alternative embodiment of a tissue-removal and medicament-delivery device of the present invention utilizing a single delivery lumen;

FIG. 36 is a schematic cross-sectional view of the embodiment of FIG. 35;

FIG. 37 is a perspective view of yet another embodiment of a tissue-removal and medicament-delivery device of the present invention utilizing a single delivery lumen;

FIG. 38 is a schematic cross-sectional view of yet another embodiment of the device of the present invention utilizing at least one vacuum lumen and at least one delivery lumen;

FIG. 39a a schematic cross-sectional view of a step of an alternate exemplary embodiment of an electrical-energy tissue-removal and medicament-delivery device of the present invention;

FIG. 39b a schematic cross-sectional view of a step of an alternate exemplary embodiment of an electrical-energy tissue-removal and medicament-delivery device of the present invention engaging tissue;

FIG. 42a is a schematic cross-sectional view yet another embodiment of a tissue-removal and medicament-delivery device of the present invention utilizing two balloons to stabilize tissue;

FIG. 42b is a schematic cross-sectional view of a step of an exemplary embodiment of a tissue-removal and medicament-delivery device of the present invention stabilizing tissue;

FIG. 42c is a perspective view of an exemplary embodiment of a tissue-removal and medicament-delivery device of the present invention having two balloons located proximate the device head;

FIG. 44a is a schematic cross-sectional view yet another embodiment of a tissue-removal and medicament-delivery device of the present invention utilizing a biasing conduit to direct the distal portion of the device;

FIG. 44b is a schematic cross-sectional view of a step of an exemplary embodiment of a tissue-removal and medicament-delivery device of the present invention utilizing a biasing conduit to direct the distal portion of the device;

FIG. 44c is a schematic cross-sectional view yet another embodiment of a tissue-removal and medicament-delivery device of the present invention utilizing a biasing conduit to direct the distal portion of the device; and FIG. 44d is a schematic cross-sectional view of a step of an exemplary embodiment of a tissue-removal and medicament-delivery device of the present invention utilizing a biasing conduit to direct the distal portion of the device.

DETAILED DESCRIPTION OF THE INVENTION

Figure 4:
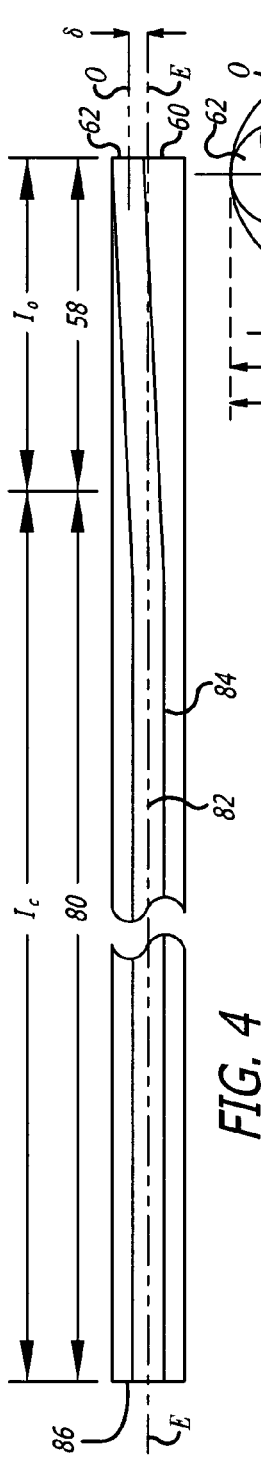
FIG. 4 is a schematic view of an exemplary optical fiber of the present invention, particularly illustrating an eccentric configuration of an outlet portion of the optical fiber.

Referring to the drawings in more detail, in FIG. 1 an exemplary embodiment of a tissue drill 50 of the present invention is illustrated in conjunction with a source of laser energy 52. Exemplary tissue drill 50 forms holes or channels in tissue by laser ablation in a consistent, controllable, and programmable manner. The first portion of the following description focuses on the principles of tissue ablation and the forming of channels in tissue. These principles of the present invention are then readily applied to a system for delivering medicaments to the tissue in which the channels are formed, which will be discussed in more detail below.

Ablation is the process of fragmenting long molecules into short gaseous molecules. Much of the tissue in living organisms, including the human body, is made up mostly of water (e.g., about 75%) with organic material making up the remaining portion. The molecules of organic material consist of atoms of carbon, nitrogen, oxygen, and hydrogen that are attached together through covalent bonds. Ablation is the process of breaking these covalent bonds. Tissue drill 50 utilizes the ablation process to break molecules of tissue apart, thereby forming holes or channels in the tissue. The ablation process will be discuss in more detail below.

Exemplary tissue drill 50 includes a handpiece 54 for manipulation by a user and an optical fiber 56, which is shown in FIG. 1A, for transmitting laser energy from laser energy source 52. Optical fiber 56 has an outlet portion 58 for emitting laser energy. Outlet portion 58 functions substantially as a drill bit. In operation, outlet portion 58 is moved from a retracted position (which is shown in the solid line) to an advanced position (which is shown by the phantom line) while emitting laser energy. Arrow A represents outlet portion 58 moving to the advanced portion, and arrow L represents laser energy emitted from outlet portion 58. Tissue is ablated by laser energy as outlet portion 58 is advanced, thereby forming a hole or a channel in the tissue. Exemplary tissue drill 50 may also rotate outlet portion 58 while moving to the advanced position, which is represented by arrow R. After reaching the advanced position, outlet portion 58 may be withdrawn to the retracted position, which is represented by arrow B. The advancing and retracting of outlet portion 58 is preferably along a central axis of optical fiber 56. Any rotation of outlet portion 58 is preferably about the central axis of optical fiber 56. The axial and rotational movement of outlet portion 58 will be discussed in more detail below.

Exemplary outlet portion 58 of optical fiber 56 has an end surface 60 with an outlet 62 from which laser energy is emitted. Outlet 62 is preferably offset from or eccentric to the central axis of outlet portion 58 so that as outlet portion 58 rotates, outlet 62 rotates about the central axis. Accordingly, laser energy emitted from outlet 62 as outlet portion 58 rotates is not focused at a single point but is rather distributed about the central axis. Alternatively speaking, the eccentric relationship of outlet 62 with respect to the central axis of outlet portion 58 preferably produces a gradient of laser energy as outlet portion 58 axially advances, with the highest level of laser energy at the central axis, which energy decreases toward a peripheral edge. The eccentricity of outlet portion 58 will also be discussed in more detail below.

Handpiece 54 may be implemented according to a variety of configurations. For example, handpiece 54 may be a flexible catheter utilized in endovascular procedures and having a plurality of lumens to facilitate visualization, flushing, and aspiration. In this regard, outlet portion 58 may advance beyond a distal end of the catheter to vascularize tissue, such as on the inside the left ventricle of the heart. Alternatively, handpiece 54 may be formed as a trocar sheath and positioned intercostally (i.e., between the ribs) for tissue access. Handpiece 54 may also be formed in a gooseneck-like configuration with a plurality of articulated joints which may be bent to assume and retain a particular shape. Moreover, handpiece 54 may be a conduit with flexible cable sheathing. Accordingly, in a general sense, handpiece 54 provides a "user interface" for delivering outlet portion 58 to a target site, which may be accomplished either by direct physical manipulation by a surgeon or by programmed mechanical control.

An exemplary handpiece of the present invention is illustrated in FIGS. 2A and 2B. Exemplary handpiece 54 may include a body portion 64 and a coupling portion 66. Exemplary body portion 64 has a distal end 68. Exemplary coupling portion 66 is adapted or configured to receive optical fiber 56 in a controlled and axially movable relationship so that outlet portion 58 may be advanced beyond distal end 68 of body portion 64. In addition, coupling portion 66 may be adapted to receive optical fiber 56 in a rotatable relationship so that at least outlet portion 58 of optical fiber 56 may rotate. If handpiece 54 is configured as a catheter or similar flexible tubular member, the inner surface of the tubular member serves as a coupling portion by receiving optical fiber 56 in a controlled, axially movable, and/or rotatable relationship.

The retracted position of outlet portion 58 as shown in FIG. 2A may be defined as a position in which end surface 60 is positioned substantially at or near distal end 68 of body portion 64. Accordingly, end surface 60 may project slightly beyond distal end 68 or, alternatively, may be either proximal to or substantially aligned (or coplanar) with distal end 68. The advanced position of outlet portion 58 as shown in FIG. 2B may be defined as a position in which end surface 60 with outlet 62 projects a distance d beyond distal end 68 of body portion 64. As will be discussed in more detail below, distance d at which end surface 60 projects beyond distal end 68 is preferably predetermined, adjustable, and/or programmable.

With additional reference to FIGS. 3A and 3B, exemplary coupling portion 66 may include a drive which is comprised of a tubular member 70 and a collar 72. Tubular member 72 receives optical fiber 56 and may have a chuck 74 for retaining optical fiber 56 thereto. Tubular member 72 may also have annular threading 76 formed along a length thereof. Collar 72 is disposed within body portion 64 and has complementary inner threading 78. Exemplary tubular member 72 is slidably and rotatably receivable within body portion 64 with annular threading 76 engaging with inner threading 78 of collar 72, as shown in FIG. 3B. Accordingly, rotation of tubular member 70 causes tubular member 70 to move axially. As optical fiber 56 is retained by chuck 74, optical fiber 56 with outlet portion 58 moves axially with tubular member 70. In an alternative embodiment of handpiece 54 such as a catheter, rather than disposing coupling portion 66 and a drive on handpiece 54, these elements may be provided at a proximal location, such as at laser apparatus 52. In this regard, catheter-configured handpiece 54 retains optical fiber 56 within a body portion which prevents buckling and which delivers outlet portion 58 to a target site but which is substantially free of coupling and drive apparatus.

Referencing FIG. 4, in addition to outlet portion 58, exemplary optical fiber 56 has an elongate portion 80. A core 82 and a cladding 84 define optical fiber 56 and extend along elongate portion 80 and outlet portion 58. Core 82 has an inlet 86 for receiving laser energy and outlet 62 (see also FIG. 1) for emitting laser energy. Core 82 and cladding 84 may be made of high-purity silica glass or sapphire, with core 82 having a higher index of refraction than that of cladding 84 so that modulated pulses of laser energy move along core 82 without penetrating cladding 84. Although optical fiber 56 may be configured according to any dimensions, for many applications a length $l_e$ of elongate portion 80 may range from about 0.5 meter (m) to more than 2 m to provide a surgeon with sufficient maneuverability, and a length $l_o$ of outlet portion 58 may range up to about 50 millimeters (mm) so that holes of different lengths may be formed in tissue. For applications other than medical, optical fiber 56 may be dimensioned accordingly to accomplish the particular application.

Figure 5:
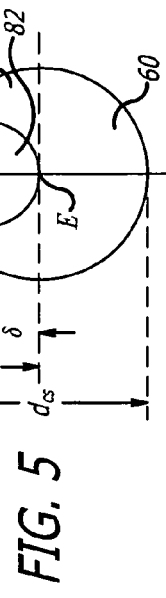
FIG. 5 is a schematic view of an end surface of the optical fiber illustrated in FIG. 4.

Core 82 of optical fiber 56 has an axis E along elongate portion 80 and an axis O at outlet 62. With additional reference to FIG. 5, core 82 along outlet portion 58 angles away from and is oblique to core 82 along elongate portion 80. At end surface 60, axis O of core 82 at outlet 62 is offset from or eccentric to axis E of core 82 of elongate portion 80 by a distance δ. Accordingly, laser energy emitted from outlet 62 is distributed about axis E as optical fiber 56 rotates about axis of rotation E. Further, the distribution of laser energy is across the entire surface area of end surface 60 as optical fiber 56 make one complete revolution. At end surface 60, outlet 62 may be configured so that axis O of core 82 is either oblique to axis E or, as shown, parallel to axis E.

Figure 6:
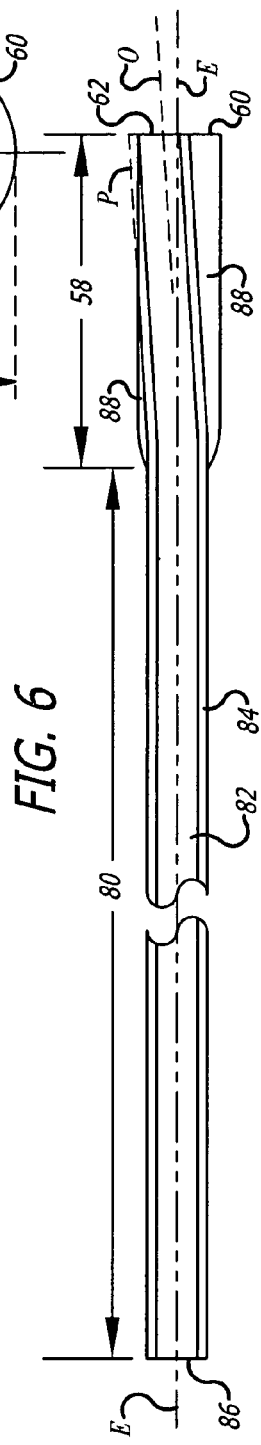
FIG. 6 is a schematic view of another exemplary optical fiber of the present invention.
Figure 7:
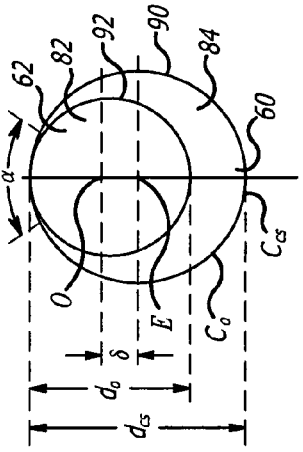
FIG. 7 is a schematic view of an end surface of the optical fiber illustrated in FIG. 6.

An alternative exemplary embodiment of optical fiber 56 is illustrated in FIGS. 6 and 7. In addition to core 82 and cladding 84, exemplary optical fiber 56 may include auxiliary cladding 88 disposed about outlet portion 58. Similar to the embodiment shown in FIG. 4, to offset axis O of outlet 62 from axis of rotation E by distance δ, core 82 of outlet portion 58 is oblique to core 82 of elongate portion 80. Auxiliary cladding 88 compensates for the oblique relationship of core 82 (and cladding 84) of outlet portion 58 with respect to core 82 (and cladding 84) of elongate portion 80. Auxiliary cladding 88 accordingly provides a preferred cylindrical configuration of outlet portion 58 so that outlet portion 58 rotates about axis E as elongate portion 80 rotates about axis E. Further, in addition to axis O at outlet 62 being eccentric to axis E, axis O of core 82 may be oblique to axis E at outlet 62, rather than a parallel relationship as shown in FIG. 4.

As illustrated in FIGS. 6 and 7, end surface 60 (including outlet 62) is substantially perpendicular to axis E of exemplary optical fiber 56. To form the perpendicular relationship, core 82 and cladding 84 are ground or polished at an angle oblique to axis O, thereby removing portions of core 82 and cladding 84 shown by phantom line P. Accordingly, exemplary end surface 60 is substantially planar. Alternatively, end surface 60 may be convex, concave, or other configuration depending upon a particular implementation of outlet portion 58.

With particular reference to FIG. 7, end surface 60 of exemplary optical fiber 56 has a circumference $C_{es}$ defined along an outer edge 90, and outlet 62 of core 82 has a circumference $C_o$ defined along outer edge 92. Circumference $C_{es}$ and circumference $C_o$ are coextensive along an arc length α of outer edges 90 and 92. This relationship allows laser energy to be emitted from outlet 62 at outer edge 90 of end surface 60. As outlet portion 58 rotates, laser energy is emitted along circumference $C_{es}$ of rotating end surface 60. Arc length α may range from a single tangent point to several seconds, minutes, or degrees as desired.

Diameter $d_o$ of outlet 62 is preferably greater than about one half of diameter $d_{es}$ of end surface 60. Accordingly, outlet 62 has a surface area which is at least one quarter of that of end surface 60. This relationship in surface area allows laser energy to be emitted from a substantial percentage of end surface 60. Further, laser energy is not emitted from the entire end surface 60 simultaneously but rather over the time it takes outlet portion 58 to make one revolution about axis E. An exemplary commercial embodiment of optical fiber 56 for use in transmyocardial revascularization entails a diameter $d_{es}$ of end surface 60 (and outlet portion 58 of approximately 1 mm and a diameter $d_o$ of outlet 62 of approximately 0.6 mm. Generally speaking, the dimensions of outlet portion 58 are determined by the type of procedure being performed and the desired size of the hole, with diameter $d_o$ of outlet 62 being at least one half of diameter $d_{es}$ of end surface 60. For example, if a hole with a 1.5-mm diameter is desired, then diameter $d_{es}$ of end surface 60 (and outlet portion 58) should be about 1.5 mm; diameter $d_o$ of outlet 62 may accordingly range from about 0.75 mm to slightly less than 1.5 mm, but is preferably about 0.8 mm. For many medical applications, it is contemplated that diameter $d_{es}$ of end surface 60 may range from about 0.2 mm to more than 2.5 mm, with diameter $d_o$ of outlet 62 ranging from less than about 0.1 mm to about 2 mm or more. For specific medical applications such as transmyocardial revascularization (which will be discussed below), diameter $d_{es}$ of end surface 60 may range from about 0.6 mm to about 2 mm, with diameter $d_o$ of outlet 62 ranging from about 0.3 mm to about 1 mm.

Figure 8:
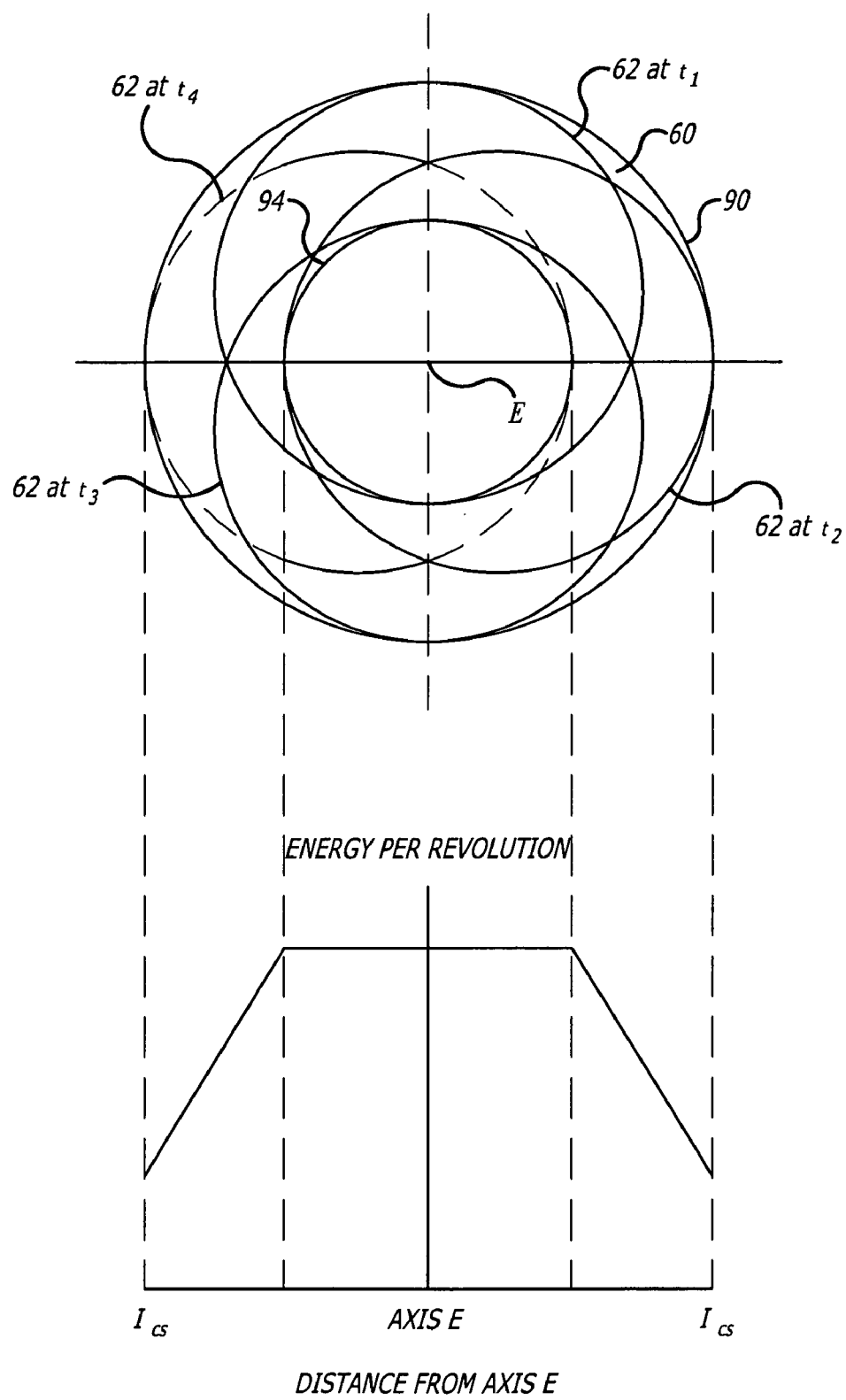
FIG. 8 is a diagrammatic view of an exemplary end surface of an optical fiber of the present invention, particularly illustrating a relationship between emitted laser energy and position of the end surface.

With additional reference to FIG. 8, end surface 60 is schematically illustrated during rotation, with outlet 62 shown at progressive instances in time $t_1$, $t_2$, $t_3$, and $t_4$ while rotating about axis E. Because of the relationship between the surface areas of end surface 60 and outlet 62, laser energy is continuously emitted from an area 94 of end surface 60. In other words, area 94 represents an intersection of the positions of outlet 62 at every instance of time while rotating about axis E. Laser energy is accordingly emitted at intervals at other areas of end surface 60 depending upon the position of outlet 62 at a particular instance in time.

The relationship between laser energy emitted from exemplary end surface 60 per revolution of outlet 62 about axis E with respect to distance from axis E is illustrated graphically in FIG. 8. Emitted laser energy per revolution of outlet portion 58 decreases from a constant level at area 94 to a lower level at outer edge 90 of end surface 60. In the graph, outer edge 90 is a distance from axis E substantially equal to radius $r_{es}$ of end surface 60. Depending upon a particular configuration of exemplary end surface 60 and outlet 62, the decrease in laser energy or flux with respect to position may be a linear function as shown or a nonlinear function. Also, the relative level of energy per revolution at area 94 and at radius $r_{es}$ is illustrative only, as the level of energy at the periphery of end surface 60 may vary according to the particular surgical procedure. For example, the energy flux at radius $r_{es}$ may be at a relatively low level when compared to the constant level at area 94.

In accordance with this energy distribution per revolution of the present invention, while ablating tissue to form a hole, the transference of laser energy to peripheral or surrounding tissue is less than at a center of the hole being formed. This distribution of laser energy may limit trauma to tissue in which holes or channels are formed. More specifically, as outlet portion 58 moves through tissue while rotating and emitting laser energy, outer edge 90 of end surface 60 is adjacent to and contacts the surrounding tissue which defines the hole being formed. As the level of emitted laser energy at outer edge 90 is lower than that centered about axis E (which essentially defines the center of the hole being formed), damage to the surrounding tissue is reduced, resulting in less trauma to the tissue. It is believed that tissue with a relatively low level of trauma has a likelihood to experience angiogenesis, or the formation of new blood vessels in the tissue. This reduced-trauma feature of the present invention will be discussed in more detail below.

An exemplary process to form an eccentric outlet portion 58 as described above involves placing the distal end of optical fiber 56 within a Teflon® tube at an angle, with cladding 84 contacting the inner surface of the tube at one point. The tube may then be filled with epoxy which surrounds the distal end of optical fiber 56 except at the point at which cladding 84 contacts the tube. After the epoxy has cured and hardened, the tube is removed, and the distal surface of the epoxy and optical fiber 56 is polished to define end surface 60 at the point where cladding 84 defines an annular edge of outlet portion 58. End surface 60 may also be formed with a lens to control the emission of the laser energy in a particular manner. An inner diameter of the tube for forming outlet portion 58 essentially determines the diameter of outlet portion 58 (i.e., diameter $d_{es}$ of end surface 60). According to this process, optical fibers 56 having outlet portions 58 of different diameters may be formed, enabling surgeons to form holes with a variety of diameters. In addition, a plurality of outlet portions 58 each having a different diameter may be formed, each of which being able to be coupled to an optical fiber, so that a set of interchangeable "drill bits" is at a surgeons disposal during a particular procedure. Optical fiber 56 may be reusable or disposable, as may outlet portion 58 and handpiece 54.

With further reference to FIGS. 1 and 3A, exemplary of handpiece 54 may include a head portion 96 connectable to a distal end of body portion 64 by a neck 98. Distal end 68 of body portion 64 is accordingly defined by a tissue end 100 of head portion 96. Exemplary head portion 96 may be conical so that tissue end 100 has a larger diameter than body portion 64. Tissue end 100 provides a working surface or a tissue-engaging surface for positioning handpiece 54 over and against a surgical site in which a channel is to be drilled into tissue. Exemplary head portion 96 may also have an aperture 102 formed therein. Aperture 102 may function as a window for viewing a surgical site when tissue end 100 is placed against tissue. Aperture 102 may also function as a vent for exhausting gases which may be generated by laser energy ablating tissue. As shown in FIG. 1, exemplary neck 98 may be angular to enhance the positioning of head portion 96 against tissue. In this regard, neck 98 may be configured as a gooseneck with articulable joints for assuming and retaining a desired shape. Exemplary head portion 96 and neck 98 are preferably tubular, thereby providing an inner continuum with body portion 64 in which optical fiber 56 is receivable.

In particular procedures, it may be preferable to know where a hole has been drilled in tissue. However, the nature of the tissue or the size of the hole may render it difficult for the surgeon to determine where a hole has already been formed. Accordingly, the newly formed hole drilled in tissue may be marked. In this regard, head portion 96 may include apparatus for marking where a hole has been drilled in tissue. For example, tissue end 100 may have an inking device which dispenses biocompatible ink or dye on the tissue where a hole has been formed. The ink may be applied to the tissue through direct contact with tissue end 100 or, for example, by spraying. Exemplary handpiece 54 may have a reservoir for storing and dispensing a colored liquid or a particulate solid to the tissue. Fluorescent material may be used to enhance visualization. Other indicia may be applied to the tissue by handpiece 54 or head portion 96 at the target site; for example, alphanumeric indicia may indicate the parameters of the laser energy emitted from outlet 62 to form a particular hole.

With further reference to FIGS. 2A to 3B, exemplary coupling portion 66 may include a spring 104 receivable against a seat 106 formed on a distal end of collar 72, and a stop 108 disposed on a distal portion of tubular member 70. Spring 104 and stop 108 define a mechanism for controlling a position of tubular member 70 within body portion 64, and may be configured to facilitate the advancement and retraction of tubular member 70.

Exemplary source of laser energy 52 is illustrated in FIG. 9. Laser energy source 52 includes a laser 110 for generating laser energy L. Exemplary laser energy source 52 may include a drive assembly 112 for operatively associating with handpiece 54 and optical fiber 56, and may also include a control unit 114 with a user interface 116. Exemplary drive assembly 112 may include a coupler 118 for connecting with optical fiber 56, optics 120 for modifying laser energy L as desired, and a drive/motor 122. Exemplary coupler 118 is associated with optics 120 for transferring laser energy L from laser 110 to the inlet of optical fiber 56. Exemplary coupler 118 is also associated with drive/motor 120 for rotating optical fiber 56.

As discussed above in reference to FIGS. 2A and 2B, exemplary coupling portion 66 of handpiece 54 translates rotational movement of optical fiber 56 to axial movement to advance and to retract outlet portion 58. Exemplary drive assembly 112 preferably rotates optical fiber 56. For example, coupler 118 may secure and retain a proximal end of optical fiber 56, with motor/drive 122 rotating coupler 118 which also rotates optical fiber 56. Drive assembly 112 may rotate optical fiber 56 in a first direction, for example, as shown by arrow $R_1$ in FIG. 2A, to cause optical fiber 56 to advance axially as shown by arrow A. When outlet portion 58 reaches the desired advanced position, drive assembly 112 may then rotate optical fiber 56 in an opposite second direction, as shown by arrow R₂ is FIG. 2B, to cause optical fiber 56 to retract axially as shown by arrow B. Exemplary drive assembly 112 may oscillate optical fiber 56 (that is, rotate optical fiber 56 clockwise and counterclockwise as shown by arrows R₁ and R₂) so that outlet portion 58 reciprocates between the retracted position and the advance position.

Exemplary laser energy source 52 preferably controls when laser energy L is emitted from outlet portion 58 of optical fiber 56. For example, control unit 114 in association with laser 110 and drive assembly 112 may limit the emission of laser energy L to only when outlet portion 58 moves to the advance position. Laser energy L may then be terminated during the retraction of outlet portion 58. Alternatively, if drive assembly 112 is reciprocating outlet portion 58, laser energy L may be transmitted only during the advancing stroke of outlet portion 58; the emission of laser energy L may then be terminated at the end of the advancing stroke. The termination of laser energy L upon reaching the advanced position is preferably automatic and controlled by laser energy source 52. Alternatively, laser energy L may be terminated by a device such as a pressure sensor which determines when the distal end of outlet portion 58 advanced completely through a section of tissue, e.g., the wall of the heart. This control of laser energy L is preferable during particular applications of tissue drill 50, which will be discussed in more detail below.

With further reference to FIG. 1A, optical fiber 56 is preferably received within a housing 124. In addition to protecting optical fiber 56, exemplary housing 124 constrains any torsional flexing or bending of optical fiber 56 which may result from the rotation by drive assembly 112. Exemplary optical fiber 56 may include a complementary coupler 126 for connecting with coupler 118 of laser energy source 52. Complementary coupler 126 preferably provides a releasable association with coupler 118 so that other optical fibers in accordance with the present invention may be connected to laser energy source 52. Exemplary housing 124 preferably extends between coupler 126 and chuck 74 of coupling portion 66 to provide integral protection of optical fiber 56 between laser energy source 52 and handpiece 54.

Exemplary laser energy source 52 may control a number of parameters of tissue drill 50, including distance d at which outlet portion 56 advances, a speed at which outlet portion 56 advances, and a level at which laser energy is emitted from outlet 62. Control unit 114 in association with user interface 116 preferably controls, programs, monitors, and/or adjusts each of these parameters depending upon a particular tissue-drilling application. For example, one the many applications of tissue drill 50 is for drilling holes or channels into or through heart walls. This procedure is known as transmyocardial revascularization or, more simply, as TMR. FIGS. 10A through 10D schematically illustrate an exemplary TMR procedure implementing tissue drill 50 of the present invention.

A heart wall 130 is illustrated in FIG. 10A and includes myocardium, or heart muscle, 132 positioned between an outer serous layer or epicardium 134 and an inner membrane or endocardium 136. It has been found to be medically beneficial to revascularize the myocardium of patients suffering from severe ischemic cardiomyopathy. The revascularization of the myocardium 132 involves forming new channels in the tissue. By implementing exemplary tissue drill 50 of the present invention, new channel may be formed in the myocardium in a controlled, consistent, and programmable manner.

Prior to a TMR procedure, the level at which laser 110 is to generate laser energy L and the frequency at which laser energy L is to be pulsed may be determined. In addition, distance d at which outlet portion 58 is to advance beyond distal end 68 and the speed at which outlet portion 58 is to rotate may be determined. These parameters may be stored in control unit 114 and varied or programmed via user interface 116.

During the TMR procedure, access to the patient's chest cavity is provided, preferably by a minimally invasive procedure such as an intercostal incision using trocar sheaths. Access to the patient's heart is then provided, for example, by incising the pericardium. With outlet portion 58 in the retracted position, a surgeon may then maneuver head portion 96 of handpiece 54 into the chest cavity and position tissue surface 100 against the epicardium 134, as shown in FIG. 10A. As discussed above, outlet portion 58 may project slightly beyond distal end 68 (that is, tissue end 100) when in the retracted position to provide the surgeon with a tactile feel of the position of end surface 60 on the epicardium 134.

When in the desired position on the epicardium 134, tissue drill 50 may be activated. This activation may be accomplished manually by an assistant via user interface 116 or by the surgeon with a foot or a hand trigger. Alternatively, activation of tissue drill 50 may be synchronized with the electrical activity of the heart through the use of an electrocardiogram (EKG) machine. Activation of tissue drill 50 causes laser energy source 52 to generate and transmit laser energy to optical fiber 56. Activation also causes optical fiber 56 to rotate and advance outlet portion 58 through the epicardium 134 and into the myocardium 132 of the heart wall 130, as shown in FIG. 10B.

Outlet portion 58 continues to advance through the myocardium 132 and through the endocardium 136. When end surface 60 of outlet portion 58 has advanced through the endocardium 136 and is positioned within the left ventricle of the patient's heart as shown in FIG. 10C, the emission of laser energy is preferably terminated, and the outlet portion 58 is retracted. A new channel 138 through the heart wall 130 results from this procedure as shown in FIG. 10D. Oxygenated blood from the left ventricle may enter the new channel 138 through the endocardium 136 and perfuse the tissue of the myocardium 132 surrounding the new channel 138. When handpiece 54 is configured as a catheter, outlet portion 58 advances through the endocardium 136 and then into the myocardium 132. Because outlet portion 58 may be programmed to advance a predetermined distance, outlet portion 58 may either continue to advance completely through the epicardium 134 or begin to retract the predetermined distance within the myocardium 132, thereby forming a hole in the heart wall 130 rather than a channel through the heart wall 130.

As mentioned above, reduced trauma to the myocardium 134 surrounding the new channel 138 results from the eccentric relationship between outlet 62 and rotational axis E. This reduced trauma may enable the surrounding tissue to regenerate vascular tissue from the new channel 138 and into the myocardium 134 or to experience angiogenesis. In addition to the eccentricity of outlet portion 58, the level of trauma inflicted on the surrounding tissue is mediated by the level of laser energy emitted from outlet 62, which will now be discussed.

With reference to FIG. 9, the energy level at which laser energy L is generated and transmitted to optical fiber 56 may be varied, programmed, and controlled according to each tissue-drilling application. For example, tissue drill 50 may be configured for drilling holes in all types of animal tissue and plant tissue, as well as other substances. The parameters which define the characteristics of laser ablation include frequency, energy per channel, pulse width, and pulse rate. As mentioned earlier, ablation is a process of breaking bonds between atoms in molecules by adding energy to the molecules. One preferred level of the laser energy L for TMR applications is to limit the energy per pulse to less than about 100 millijoules per square millimeter of area (mJ/mm$^2$). More preferably, an energy per pulse of about 30 mJ/mm$^2$ has been found to ablate cardiac tissue at a substantially reduced level of trauma. The energy per pulse of laser 110 may be varied according to specific tissue-drilling procedures.

With further reference to FIGS. 3A and 3B, the drive may be configured to control the rate at which outlet portion 58 advances and retracts. The rate of advancement is controlled by the speed at which optical fiber 56 rotates and the pitch of the complementary threading of collar 72 and tubular member 78. For smooth and continuous operation, it has been determined that optical fiber 56 and, accordingly, outlet portion 58 should rotate at a speed under about 5,000 revolutions per minute (RPM). For TMR applications of tissue drill 50, a rotational speed ranging from about 1,000 RPM to about 2,000 RPM is preferred. In this regard, a specific TMR configuration of tissue drill 50 may be as follows. Optical fiber 56 may rotate at about 1,340 RPM. The pitch of threading 76 and 78 may be configured so that outlet portion 58 advances at a rate of about 15.5 millimeters per second (mm/s). With a rotational speed of 1,340 RPM, it takes about 46 milliseconds (ms) for outlet portion 58 to complete one rotation. For TMR applications, laser 110 may emit pulses of laser energy L of about 20 nanoseconds (ns) in duration, with each pulse being separated by about 4 ms. The pulse rate may be about 10 pulses per revolution (or at about every 36° of rotation) or about 240 pulses per second.

Rather than advancing and retracting outlet portion 58 at a constant rate as described above, tissue drill 50 may be configured such that outlet portion 58 moves at varying rates of speed between the retracted and advanced positions. The slower outlet portion 58 advances (or retracts) while emitting laser energy L, the more tissue that becomes ablated because the tissue is subject to more laser energy over time. Accordingly, a hole may be formed with a diameter greater than diameter $d_{es}$ of end surface 60 (and outlet portion 58) by advancing outlet portion 58 at a speed which allows laser energy L to ablate a greater amount of tissue. Alternatively, the power of laser energy L may also be varied during the advancement of outlet portion 58 so that the tissue is subjected to more or less laser energy L. Generally speaking, a surgeon may program tissue drill 50 to ablate tissue at varying levels of energy per unit time to form holes of varying desired diameters or configurations. The energy per unit time may be adjusted by varying either the speed at which outlet portion 58 advances (which varies the time the tissue is subject to laser energy) or the level of laser energy, or both.

In order to form the substantially cylindrical hole 138 shown in FIG. 10D, tissue drill 50 advanced outlet portion 58 at a substantially constant speed, and laser energy source 52 emitted laser energy at a substantially constant level. However, if a conical-shaped hole 140 as shown in FIG. 11 is desired, with the apex of the hole 140 positioned at the epicardium 134 and the base of the hole 140 positioned at the endocardium 136, then tissue drill 50 may be configured to advance outlet portion 58 at a decreasing rate (i.e., moving at a slower and slower speed) while advancing through the heart wall 130 from the epicardium 134 to the endocardium 136. Accordingly, a greater amount of tissue is ablated as outlet portion 58 advances at a slower speed. The resulting hole 140 has a diameter substantially equal to diameter $d_{es}$ of outlet portion 58 at the epicardium 134 and a diameter larger than diameter $d_{es}$ at the endocardium 136. By forming the hole 140 with a relatively large diameter at the endocardium 136 improves the patency of the hole and, therefore, the perfusion of the blood into the myocardium 132. In addition, by forming a hole with as small a diameter as possible at the epicardium 134 minimizes bleeding and trauma.

With reference to FIG. 12, another noncylindrically shaped hole 142 is shown. Rather than forming hole 142 by advancing outlet portion 58 from the epicardium 134 to the endocardium 136 as shown in FIG. 11, hole 142 is formed endovascularly, with outlet portion 58 advancing from the endocardium 136 and into the myocardium 132 a predetermined distance d. As mentioned above, to form holes endovascularly, handpiece 54 may be configured as a catheter, with access to the left ventricle of the heart provided through, for example, a femoral artery and the aorta. To form hole 142 with a diameter greater than diameter $d_{es}$ of end surface 60 at the endocardium 136, tissue drill 50 is configured to advance outlet portion 58 relatively slowly at or near the epicardium 136 and then to increase the speed. This results in more tissue being ablated at or near the endocardium 136 than at the "bottom" of hole 142 within the myocardium 132. Laser energy may also be emitted while outlet portion 58 retracts to ablate more tissue toward the endocardium 136. The speed of advancement may be varied by varying either the revolutions per second at which outlet portion 58 rotates or the pitch of threading 76 and/or 78, or both. As mentioned above, rather than varying the speed at which outlet portion 58 advances, the level of emitted laser energy L may be varied. In this regard, to form hole 142, tissue drill 50 may be configured to emit laser energy L at a relatively high level when outlet portion 58 begins to advance, and then to decrease the level as outlet portion 58 advances distance d.

Alternatively, rather than adjusting the speed or the energy level, outlet portion 58 may reciprocate a multiple of times either at increasing depths or at decreasing depths. For example, referencing FIG. 12, if the desired depth of the hole to be formed is distance d (that is, the distance end surface 60 advances beyond the distal end of handpiece 54), then tissue drill 50 may be configured to advance outlet portion 58 a distance d on a first stroke and then to advance outlet portion 58 a distance which incrementally decreases for each subsequent stroke for a predetermined number of strokes. Accordingly, even though the speed at which outlet portion 58 advances and the level at which laser energy L is emitted, hole 142 may be formed with a relatively large diameter at the endocardium 136 and tapered toward the epicardium 134 because tissue toward the endocardium 134 is subject to repeated laser energy with the multiple strokes of outlet portion 58. Therefore, a greater portion of this tissue is ablated because of the increased level of energy received per unit time. Alternatively, rather than decreasing the distance of the stroke, the distance of each multiple stroke may be incrementally increased to form hole 140 of FIG. 11. In addition, if it is desired to form a hole with a relatively large-diameter inner chamber, then tissue drill 50 may pause outlet portion 58 at a predetermined distance for a predetermined amount of time to concentrate laser energy at one location to ablate a relatively large portion of tissue at that location.

Delivery of Medicament to Tissue

Figure 13:
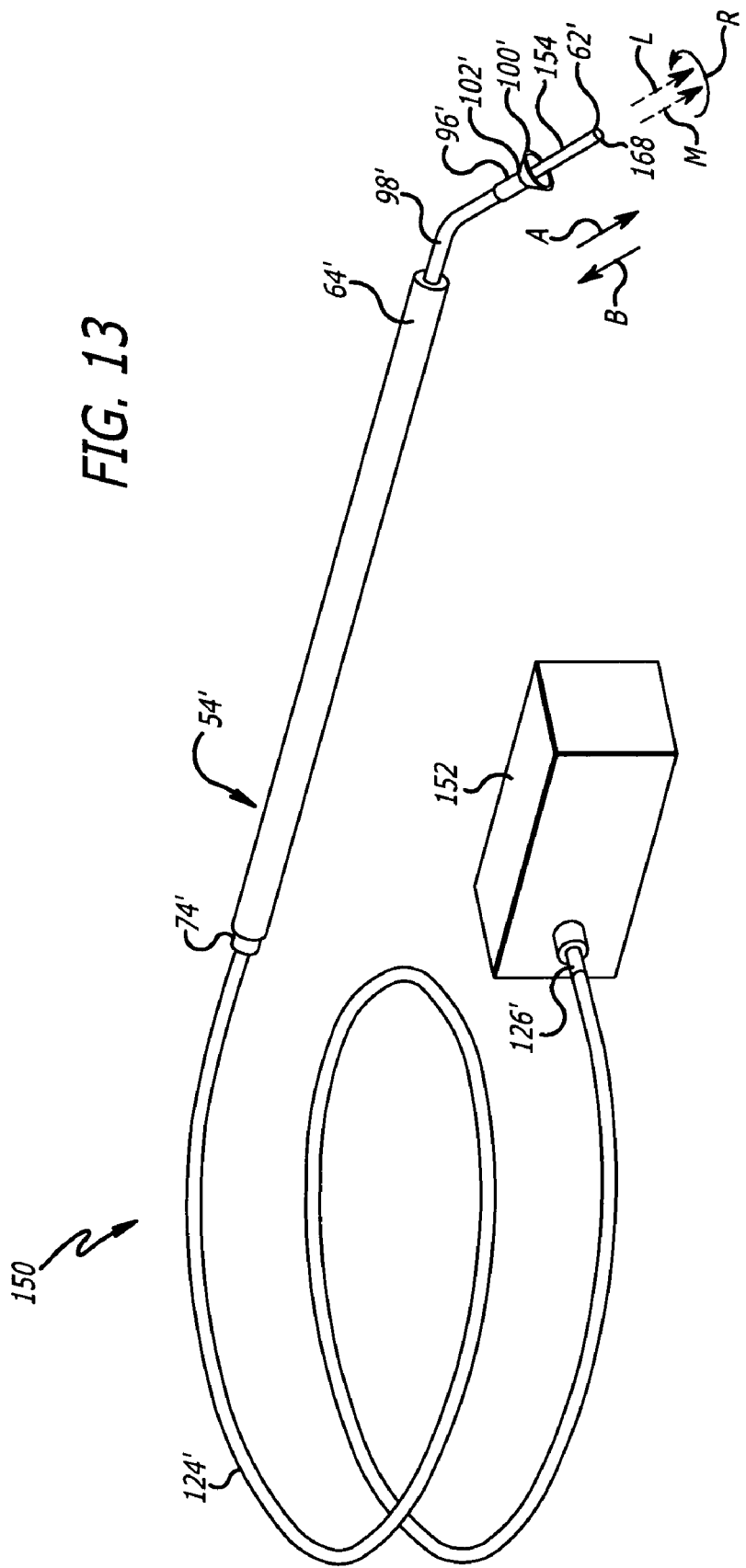
FIG. 13 is a perspective view of an exemplary medicament delivery system configured in accordance with the present invention.

An exemplary system for delivering medicament to tissue which is configured in accordance with the present invention is illustrated in FIG. 13. Exemplary medicament delivery system is referenced with numeral 150 and may be utilized to form a hole or channel in tissue, for example, cardiac tissue (myocardium), and then to deliver medicament, for example, a therapeutic agent for the treatment of cardiovascular disease, or a growth factor, to the tissue by partially or fully filling the hole or channel with the medicament, by injecting medicament into the tissue surrounding the hole or channel, or by administering medicament to a region which includes the hole or channel and the surrounding tissue. This process may be repeated to form and fill a plurality of holes and channels in a targeted area of tissue. In contrast to conventional systemic delivery approaches, the system 150 of the present invention delivers medicament in a controlled manner to specific targeted tissue. The terms hole, pocket, and channel used herein indicate any space formed in tissue or through a section of tissue, which space may be substantially regular in shape, such as circular, elliptical, curvilinear, or rectilinear, or substantially irregular in shape.

The exemplary embodiment of delivery system 150 illustrated in FIG. 13 forms the holes or channels by removing or displacing tissue with laser ablation. As mentioned above, it has been found that tissue ablation with laser energy stimulates a natural biological process of angiogenesis in the heart. In addition, a plurality of medicaments may be delivered to the ablated regions to enhance biological response and increase the therapeutic effect. For example, angiogenic-enhancing growth factors have been found to promote angiogenesis in the heart. Accordingly, a synergistic stimulation and promotion of angiogenesis in the heart is created by augmenting the heart's natural angiogenic response to laser ablation with the delivery of growth factor to those areas of the myocardium which have been ablated. The coupling of the heart's natural response to the formation of channels with the delivery of angiogenic growth factor into or adjacent to those channels provides a benefit to patients not possible prior to the present invention.

Medicament delivery system 150 may include many of the same elements as exemplary tissue drill 50 discussed above. Elements of medicament delivery system 150 which are substantially analogous to elements of tissue drill 50 use like reference numerals with the addition of a prime ('). For example, medicament delivery system 150 includes a handpiece 54' which may be substantially the same as handpiece 54 of tissue drill 50. This referencing convention will be used in the description hereunder, and the earlier description of such analogous elements will not be repeated in connection with medicament delivery system 150.

In cardiac applications of the system 150 of the invention, the administration of medicament such as endothelial growth factor to cardiac tissue such as myocardium promotes cardiovascular angiogenesis. Growth factors are proteins that stimulate or enhance cell growth. Growth-factor proteins may be packaged in carrier molecules to specifically enhance angiogenesis. For example, the naked DNA of the growth-factor protein may be combined with a cellular matrix. Examples of cellular matrixes include fibrin, plasma, and any other structure that enhances the biocompatibility of the growth factor in the tissue, the angiogenic activity of the growth factor, and/or the sustained release of the growth factor into the tissue. There are many commercially available growth factors that promote angiogenesis, such as vascular endothelial growth factor (VEGF), basic fibroblast growth factor (bFGF), transforming growth factor-beta (TGF-β), and platelet-derived growth factor (PDGF). The term medicament used herein may include growth factor alone, growth factor in combination with a cellular matrix, or growth factor in combination with any other component that is known to assist in the delivery of the growth factor. In addition, medicament could include any other substance that stimulates angiogenic activity in the heart. In an alternate embodiment, the medicament may further include or otherwise incorporate radio-opaque material to assist in precisely delivering and applying the medicament.

To deliver medicament to myocardium, exemplary medicament delivery system 150 includes a tissue-removal device for forming holes or channels in tissue, such as a source of laser energy and medicament 152 and an ablating and injecting device 154. As discussed in more detail below, ablating and injecting device 154 includes an optical fiber which receives laser energy from source 152 for ablating tissue to form a channel, and a delivery member which receives medicament from source 152 for injection into the channel. In cardiac applications, system 150 is able to deliver growth factor directly into the ischemic myocardium of a patient to promote the growth of endothelial cells.

With additional reference to FIGS. 14 and 15, exemplary ablating and injecting device 154 may include an optical fiber 156 and a delivery member 158 molded together into a unitary structure with cladding 160. As described above, exemplary optical fiber 156 may include a core 82' and a cladding 84', with core 82' having an inlet 86' for receiving laser energy and outlet 62' for emitting laser energy, as indicated by arrow L in FIG. 13. Exemplary delivery member 158 may include a wall 162 in which is defined a lumen 164 with an inlet 166 for receiving medicament and an outlet 168 for providing medicament, which is indicated by arrow M in FIG. 13. Ablating and injecting device 154 has an end surface 170 and an outlet portion 172. Outlets 62' and 168 may be substantially coplanar with end surface 170.

Figure 16:
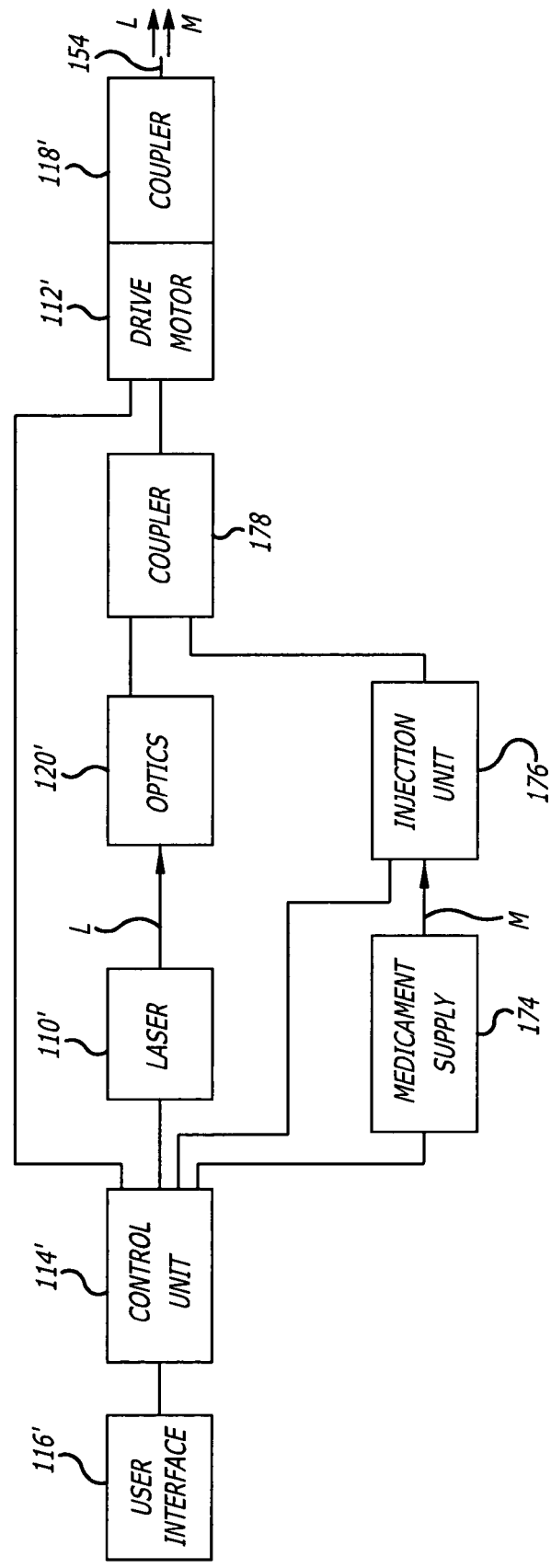
FIG. 16 is a schematic view of an exemplary source of laser energy and medicament for use in the medicament delivery system of the present invention.

Referencing FIG. 16, exemplary laser energy and medicament source 152 may include a laser 110', a drive motor 112', a control unit 114', a user interface 116', and a coupler 118' as described above. Source 152 may also include a medicament supply 174 for providing medicament M and an injection unit 176 connected to supply 174, both of which are connected to control unit 114'. A coupler 178 connects lines from laser optics 120' and injection unit 176 into the unitary ablating and injecting device 154.

Analogous to optical fiber 56 described above, exemplary ablating and injecting device 154 is rotatable about an axis of rotation E and translatable between an advanced position and a retracted position. With additional reference to FIGS. 17A and 17B, system 150 may form a channel 138 in myocardium 132, either partially through the myocardium or completely through the myocardium. In accordance with the present invention, as distal portion 172 of ablating and injecting device 154 retracts from the advanced position to the retracted position, as shown by arrow B, control unit 114' activates injection unit 176 to inject medicament M from supply 174 into delivery member 158 and through outlet 168 into channel 138, as shown in FIG. 17A. When device 154 is in the retracted position and handpiece 54' is moved away, a discrete amount 179 of medicament is left within channel 138, as shown in FIG. 17B. The discrete amount 179 may partially or fully fill channel 138. The procedure may be repeated a plurality of times at different locations in the myocardium 132, thereby seeding the myocardium with medicament such as angiogenesis-promoting growth factor. Exemplary injection unit 176 may inject medicament through the use of hydraulics, pneumatics, aerosol, or other means.

In addition, injection unit 176 may be configured as an injection jet nozzle which utilizes high pressure to create a fluid column of medicament for injection into tissue. A jet injector may also be used to form a hole in or through tissue with high-pressure fluid (which may contain medicament), either by tearing (or expanding) the tissue or by removing or displacing the tissue, or a combination of both. The jet injector may be configured to deliver medicament to the tissue while forming the hole or channel therein.

Regarding the coupling of ablating and injecting device 154 to laser energy and medicament source 152, reference is made to FIGS. 18 and 19 in which an exemplary embodiment of a coupling assembly 180 is illustrated. Exemplary coupling assembly 180 includes a housing 182 which is adapted to receive a reel 184 in a rotatable and sealed relationship. Reel 184 includes a passage 186 formed axially therethrough in which ablating and injecting device 154 is securely received. Reel 184 also includes an annular channel 188 and a through hole 190 extending between passage 186 and channel 188. Delivery member 158 extends from device 154 into through hole 190 to be in communication with channel 188. A feeding tube 192 extends between a port 194 of housing 182 and the medicament injection and supply units 176 and 174.

A plurality of o-rings 196 may be used to seal reel 184 within housing 182, device 154 within passage 186, and delivery member 158 within through hole 190. Rings 196 may be low-friction Teflon® seals. Specialized couplings, such as a Touhy-Borst valve coupling, may be used to connect device 154 to reel 184. Housing 182 may include structure such as stops to limit the axial translation of reel 184. Although exaggerated in the drawings, tolerances between reel 184 and housing 182 may be on the order of less than about 0.005 inch. In addition, housing 182 may be of a two-piece design with two halves hinged together to allow easy access to the inside of the housing.

Coupling assembly 180 allows ablating and injecting device 154 to rotate about rotational axis E under power from drive unit 112' while receiving laser energy and medicament. For example, device 154 may be driven about 40 revolutions in one direction (yielding the advanced position), and then driven about 40 revolutions in the other direction (yielding the retracted position). Because of the secure coupling with device 154, reel 184 is driven by device 154 to rotate about axis E, that is device 154 may act as a drive shaft. When it is desired to deliver medicament to tissue, injection unit 176 injects medicament through tube 192 (which is indicated by arrow M) and into a space 198 defined within channel 188 and between reel 184 and housing 182. Medicament is accordingly urged and/or injected into the lumen 164 of delivery member 158. Medicament may be continuously injected into delivery lumen 158 while reel 184 rotates. As described above, the injection of medicament into delivery lumen 158 may be limited to when device 154 is retracting.

With general reference to FIG. 13, rather than coupling delivery member 158 to medicament supply 174 at source system 152, exemplary handpiece 54' may include an assembly for injecting medicament into delivery member 158 (not shown). For example, a pressure capsule, such as a $CO_2$ capsule, may inject medicament into the inlet 166 of lumen 164 and out of the outlet 168. Delivery member 158 may be coiled within handpiece 54' when in the retracted positioned, and may then uncoil while being driven to the advanced position. In the embodiment with an injection assembly at handpiece 54', delivery member 158 may have a relatively short overall length as the handpiece is positioned at or near the tissue targeted to receive medicament.

Alternative configurations of the ablating and injecting device of the present invention are shown in FIGS. 20 and 21. Referencing FIG. 20, exemplary ablating and injecting device 154' includes an optical fiber 156' and a delivery member 158' molded together into a unitary structure with cladding 160'. Exemplary delivery member 158' may be crescent shaped in cross-section, as shown. As discussed above, the diameter $d_o$ of the outlet of optical fiber 156' is preferably at least one half of the diameter $d_{es}$ of the end surface 170' of device 154'. For example, diameter $d_o$ may be about 0.6 mm and diameter $d_{es}$ may be about 1.0 mm. Accordingly, as device 154' rotates about axis E, laser energy emitted from optical fiber 156' ablates tissue along the entire radial sweep of axis E, thereby forming a channel of about 1.0 mm in diameter, which is described above (see FIG. 8).

Referencing FIG. 21, exemplary ablating and injecting device 154" includes a pair of optical fibers 156a and 156b and a delivery member 158" molded together into a unitary structure with cladding 160". Exemplary delivery member 158" may be rectilinear shaped in cross-section, as shown. The outlet of each optical fiber 156 preferably has a diameter $d_o$ of approximately one quarter of the diameter $d_{es}$ of the end surface 170" of device 154'. Therefore, collectively the diameters $d_o$ of the optical fibers 156a and 156b comprise about one half of the diameter $d_{es}$ of the end surface 170". For example, diameter $d_o$ may be about 0.3 mm and diameter $d_{es}$ of end surface 170" may be about 1.0 mm. Alternatively, any number of fibers may be used in multiple-fiber device 154", such as four 0.15-mm diameter fibers.

Optical fiber becomes more flexible when its diameter is reduced. It follows that the pair of optical fibers 156a and 156b of FIG. 21 each with a diameter of about 0.3 mm are more flexible than the single optical fiber 156' of FIG. 20 with a diameter of about 0.6 mm. As such, device 154" is more flexible and is able to follow a more tortuous path than device 154'. Accordingly, device 154' shown in FIG. 20 is useful in direct-visualization procedures in conjunction with a handpiece as described above, such as in intra-operative or trans-thoracic procedures, which do not require the optical fiber to bend through tortuous paths. Device 154" shown in FIG. 21 is useful in indirect-visualization procedures in conjunction with a catheter and a scope, such as trans-septal and endovascular procedures. For example, device 154" may be inserted into a femoral artery, through the aortic arch, and into the left ventricle to ablate tissue from the endocardium to the epicardium.

Rather than forming channels in tissue with laser ablation as described above, tissue may be removed or displaced to form channels in accordance with the present invention for medicament delivery by other methods, for example, by high-frequency electrical energy or radio-frequency (RF) energy. Referencing FIG. 22, an exemplary embodiment of a tissue-removal and medicament-delivery device 200 which uses electrical energy to remove or displace tissue in accordance with the present invention is illustrated. Device 200 includes an electrode 202 disposed on a distal tip of the device, an insulator 204 proximal to the electrode 202, and a body 206. A delivery lumen 208 is formed axially through electrode 202, insulator 204, and body 206, and has an outlet 210 in a distal end of device 200.

An alternative embodiment of an electrical-energy tissue-removal and medicament-delivery device 200' of the invention is illustrated in FIG. 23. Rather than having an axial delivery lumen, device 200' includes at least one delivery lumen 210 formed longitudinally through at least the body 206'. As shown in FIG. 23, two delivery lumens 212a and 212b are formed through the body 206' and extend into the insulator 204'. Each lumen 212 has an outlet 214 formed on a side 216 of device 200'. In the exemplary embodiment, outlets 214a and 214b may be substantially diametrically opposed within the device. Alternatively, each lumen 212 may have a plurality of outlets which form an array of ports on the side 216 of device 200'.

With additional reference to FIG. 24, in use, the tissue-removal and medicament-delivery devices 200 and 200' generate high-frequency electrical energy, which in turn generates an ionized plasma corona 216 and converts tissue 132 to gas to create a channel or hole in the tissue. A ground plate 218 may be provided such that tissue 132 is positioned between the ground plate and electrode 202. The ground plate 218 may be used to control conduction paths (shown by the dashed arrows) formed by the positively charged electrode 202, which controls the formation of channels in tissue. After holes or channels are formed in tissue, medicament such as growth factor that promotes angiogenesis may be delivered to the tissue within the hole or channel itself via the delivery lumen as described above. Alternatively, with reference to FIG. 25, medicament may be delivered into the walls of the hole or channel 138 and into the tissue 132 surrounding the hole or channel 138 via the delivery lumens 212, as indicated by arrows M.

Referencing FIG. 26, another exemplary embodiment of an electrical-energy tissue-removal and medicament-delivery device 200" of the invention is illustrated. Device 200" includes a cathode 220 disposed on a distal tip of the device, an insulator 204" proximal to the electrode 202, an anode 222 proximal to the insulator, and a body 206". A delivery lumen 208 is formed axially through the device 200". Electrical-conducting leads (not shown) connect the cathode and anode 220 and 222 to a power source. When activated, conduction paths (shown in dashed lines) between the cathode 220 and the anode 220 define the ionized plasma cornea 216' which converts tissue to gas to form channels.

Another exemplary embodiment of a medicament-delivery system 230 of the present invention is illustrated in FIGS. 27, 28, and 29. System 230 includes an ablating and injecting device 232 received within a catheter 234. Exemplary ablating and injecting device 232 includes a pair of optical fibers 236a and 236b and a pair of delivery members 238a and 238b. Cladding 240 configures the fibers 236 and 238 into a unitary and cylindrical device. Optical fibers 236 and delivery members 238 may be configured and function in accordance with the description provided above. Exemplary device 232 also includes rifling tracks 242 formed on an annular lip 244 thereof, preferably at a distal end of the device, and exemplary catheter 234 includes rifling 246 formed on an inner surface thereof for slidingly engaging with the rifling tracks 242 of the ablating and injecting device 232. Accordingly, as ablating and injecting device 232 rotates, the rifling 246 translates the device 232 axially within catheter 234, between the advanced and retracted positions as described above.

Exemplary medicament-delivery system 230 is particularly useful in endovascular procedures which may entail guiding the ablating and injecting device 232 and catheter 234 through tortuous paths to its final destination. Accordingly, it is preferable to maximize as much as possible the flexibility of the ablating and injecting device 232. As such, it is preferable for the diameters of the optical fibers 236 to be as small as possible while still capable of carrying sufficient laser energy to ablate tissue. In a preferred embodiment, the diameter of each optical fiber 236 may be about 0.25 mm. The overall diameter of the device 232 may then be about 0.5 mm.

In an alternative embodiment of the ablating and injecting device of the present invention, the medicament may be delivered directly to the tissue surrounding the channel instead of delivering the medicament into the channel or into the tissue by way of the channel. This may be advantageous where it is desirable to avoid systemic administration of the medicament, which could occur through washout of medicament when it is delivered directly into the channel. Various configurations of this alternate embodiment are shown in FIGS. 30-40.

Figure 30:
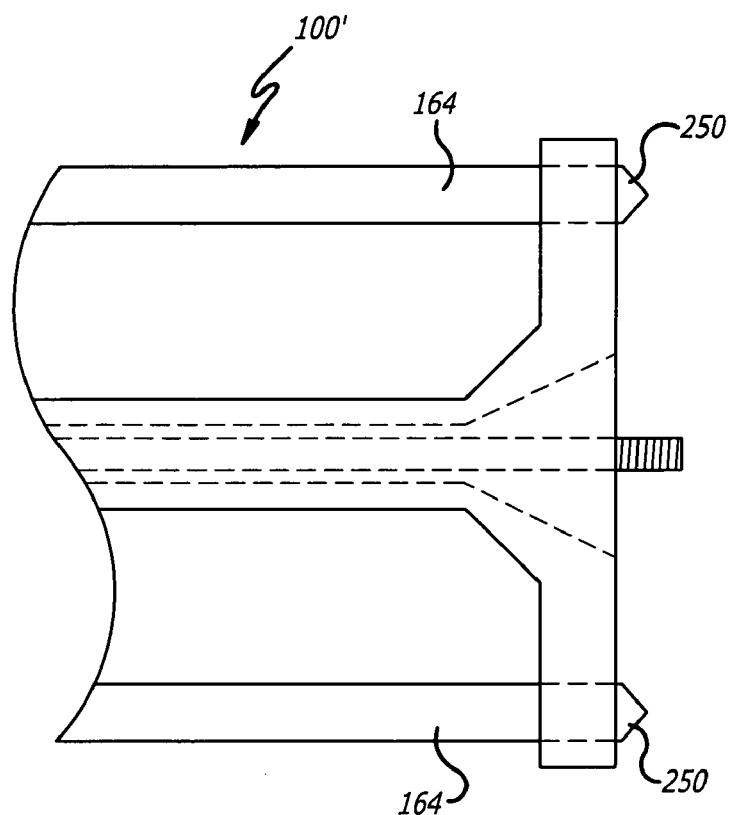
FIG. 30 is a schematic view of an exemplary medicament delivery system of the present invention, illustrating needles around the perimeter of the head portion of the handpiece.

Referencing FIG. 30, alternate head portion 100' has one or more needles 250 on the outer rim of its tissue-engaging surface for penetrating the tissue around the perimeter of the tissue channel opening. This provides access directly to the tissue surrounding the channel. The delivery device is provided with one or more medicament lumens 164' which are in fluid communication with needles 250. Needles 250 pierce the tissue around the perimeter of the channel opening and deliver medicament by way of lumen or lumens 164'. The medicament diffuses through the tissue without having to enter into the channel, thus avoiding medicament washout and the possibility of systemic delivery of the medicament. FIG. 31 illustrates the end surface of head portion 100' having an array of needles 250 around its perimeter. FIG. 32 illustrates medicament 252 diffusing into the tissue surrounding channel 138.

Figure 33:
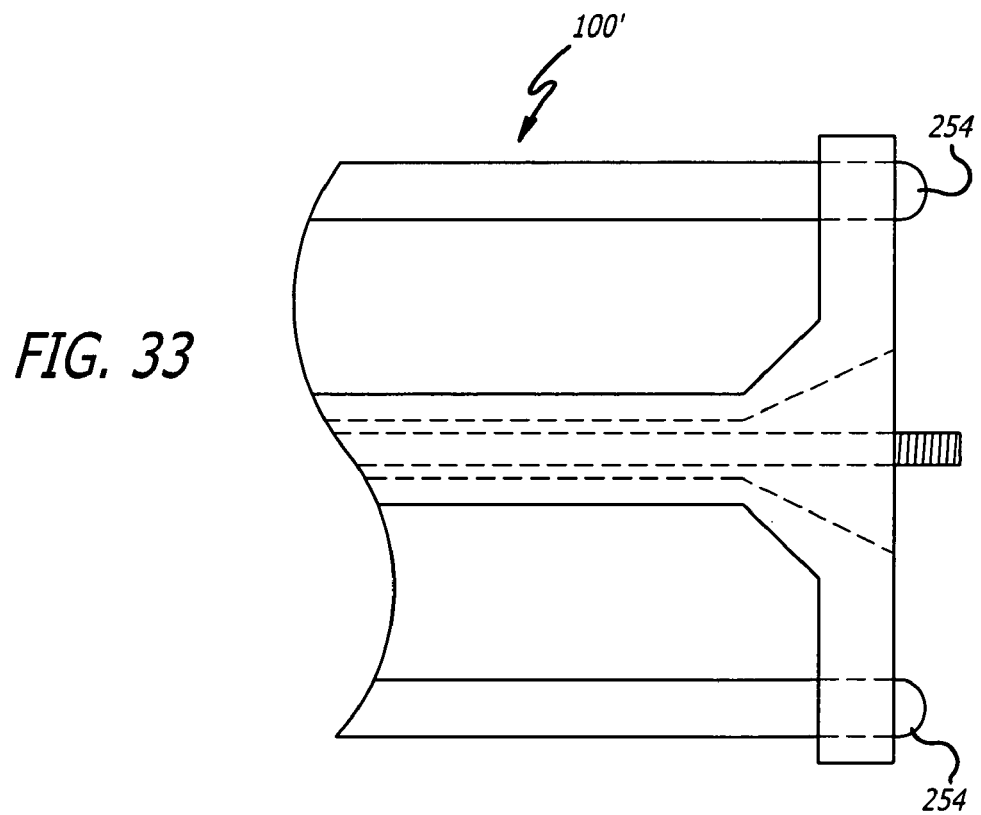
FIG. 33 is a schematic view of another exemplary embodiment of the head portion of the handpiece, illustrating nozzles around the perimeter of the head portion of the handpiece.

Other embodiments of alternate head portion 100' are illustrated in FIGS. 33 and 34. FIG. 33 illustrates head portion 100' having a nozzle or nozzles 254 around its perimeter. Nozzles 254 are adapted to atomize the medicament when head portion 100' is placed up against the tissue surrounding the channel opening. As in the previous embodiment using needles 250, the medicament is diffused directly into the tissue and not into the channel where it can be washed out into the patient's system. FIG. 34 illustrates yet another embodiment wherein head portion 100' has a port or ports 256 on the head portion perimeter for diffusing medicament directly into the tissue surrounding the channel opening.

FIGS. 35 and 36 illustrate that medicament can be provided to head portion 100' through a single lumen 164" which is in fluid communication with an annular manifold 258 which communicates through the perimeter of head portion 100' to ports 256. FIG. 37 illustrates an alternate embodiment wherein single lumen 164" has an annular geometry. Those skilled in the art will appreciate that this single lumen embodiment incorporating manifold 258 can also be utilized with nozzles 254 or needles 250. Similarly, it will be appreciated by those skilled in the art that other means for diffusing medicament directly into the tissue surrounding the channel opening can be utilized for like effect.

FIG. 38 illustrates yet another exemplary embodiment wherein at least one delivery lumen 264 is in fluid communication with delivery outlet 266 and at least one vacuum lumen 268 is in communication with a vacuum source (not shown) and terminates in vacuum outlet 270. By providing a vacuum to head portion 100' through lumen 268 to outlet 270 the clinician can insure that medicament can be delivered directly to the tissue through lumen 264 and outlet 266. It will be appreciated by those skilled in the art that this embodiment could include a plurality of vacuum lumens and a plurality of delivery lumens to maximize the effectiveness of the invention.

Referencing FIG. 39a-b, an alternate exemplary embodiment of an electrical-energy tissue-removal and medicament-delivery device 200" is illustrated wherein the medicament can be directly delivered into the tissue walls and diffused into the tissue surrounding the channel. As in the embodiment of FIG. 23, two delivery lumens 212a' and 212b' are provided, each having its respective outlet 214a' and 214b'. In the exemplary embodiment, outlets 214a' and 214b' may be substantially diametrically opposed within the device. In this embodiment, vacuum lumens 212c' and 212d' are provided longitudinally through the body of device 200" and in communication with outlets 214c' and 214d', respectively. Outlets 214c' and 214d' may also be diametrically opposed to each other. Vacuum lumens 212c' and 212d' are in communication with a vacuum source (not shown) which provides a vacuum through lumens 212c' and 212d' to outlets 214c' and 214d' to draw the tissue channel wall up against outlets 214c' and 214d'. Due to their proximity, sufficient vacuum can be provided to also draw the tissue wall up against outlets 214a' and 214b'. Medicament 252 can then be provided through delivery lumens 212a' and 212b' to outlets 214a' and 214b' and directly into the tissue wall of the channel as illustrated in FIG. 40. In the embodiment shown, outlets 214a' and 214b' are distal to outlets 214c' and 214d'. However, it is also possible to configure the outlets so that 214c' and 214d' outlets are distal to 214a' and 214b' outlets and to configure the delivery and vacuum lumens accordingly. As is the case with the embodiment of FIGS. 30-38, this embodiment also permits medicament to be diffused into the tissue surrounding the channel without having systemic washout of the medicament. FIG. 39B shows the present embodiment engaging tissue.

Figure 40A:
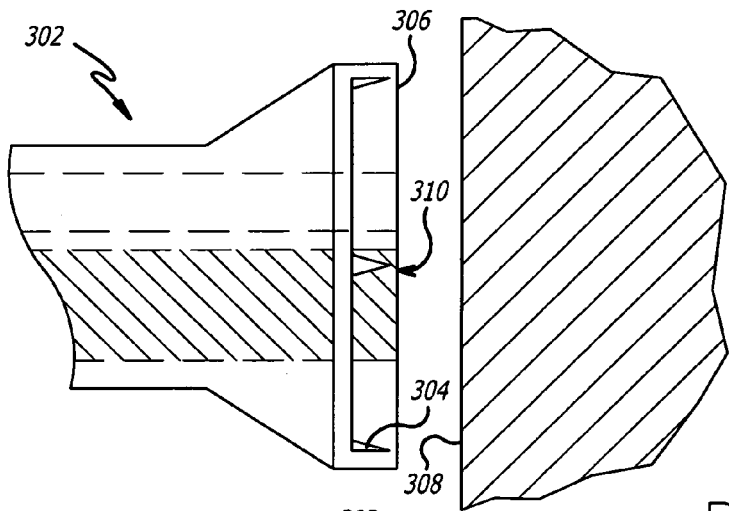
FIG. 40a is a schematic cross-sectional view of a step of yet another embodiment of a tissue-removal and medicament-delivery device of the present invention having deployable tissue stabilizers retracted within the device head.
Figure 40B:
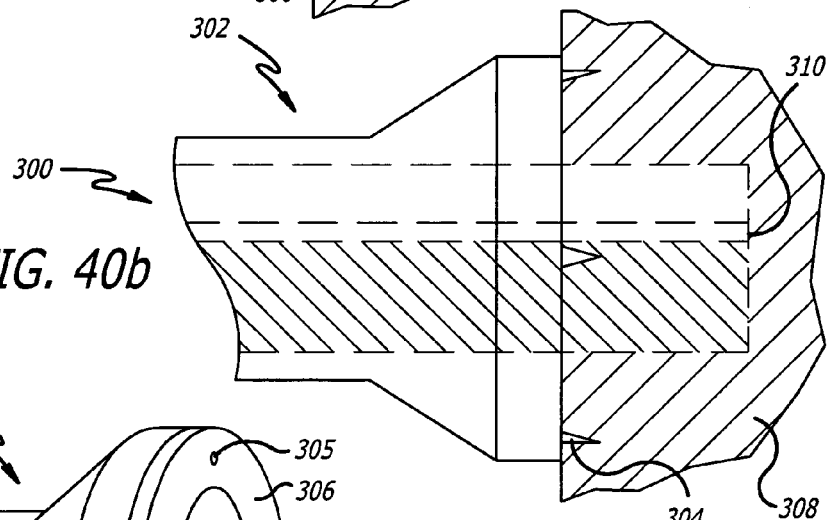
FIG. 40b is a schematic cross-sectional view of a step of an exemplary embodiment of a tissue-removal and medicament-delivery device of the present invention having deployable tissue stabilizers engaging tissue.
Figure 40C:
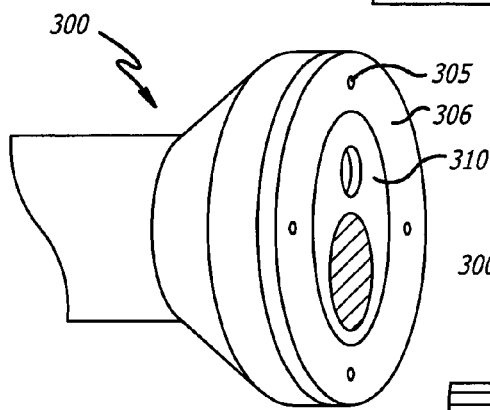
FIG. 40c is a perspective view of an exemplary embodiment of a tissue-removal and medicament-delivery device of the present invention having deployable tissue stabilizers retracted within the device head.

As illustrated in FIG. 40a-40d, an alternate exemplary embodiment of the ablating and injecting device 300 of the present invention is contemplated, wherein an alternate head portion 302 comprises at least one deployable tissue stabilizer 304 positioned within a stabilizer receiver 305 located on the outer rim of its tissue-engaging surface 306. As shown in FIG. 40a, the device 300 having the at least one deployable tissue stabilizer 304 positioned within the head portion 302 is advanced to a position proximate the tissue 308. In the illustrated embodiment, the tissue stabilizer 304 comprises tissue penetrating members, needles, or barbs. Those skilled in the art will appreciate that the tissue stabilizer 304 could also comprise vacuum attachment systems, balloon devices, and extendable wire tissue supports. The at least one tissue stabilizer 304 is deployed and the device is advanced such that the at least one tissue stabilizer engages the tissue 308. Thereafter, the ablation member 310 is advanced into the tissue 308. FIG. 40b shows the at least one deployable tissue stabilizer 304 deployed through the stabilizer receiver 305 as the tissue-engaging surface 306 engages the tissue 308, thereby resulting in the device 300 being anchored to the tissue 308. FIG. 40c shows the head portion 302 having the stabilizer receivers 305, the tissue-engaging surface 306, and a tissue ablating member 310.

Figure 40D:
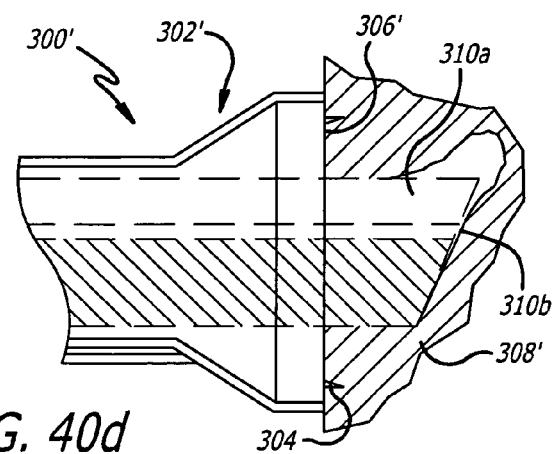
FIG. 40d is a perspective view of an exemplary embodiment of the medicament-delivery device of the present invention having an angular reflector capable of forming traverse or angular holes, pockets, or channels in tissue.

FIG. 40d shows an alternate exemplary embodiment of the ablating and injecting device 300' of the present invention. As shown in FIG. 40d, the ablating and injecting device 300' comprises an alternate head portion 302' including at least one deployable tissue stabilizer 304' positioned within a stabilizer receiver 305' located on the outer rim of its tissue-engaging surface 306'. As shown, the device 300' having the at least one deployable tissue stabilizer 304' positioned within the head portion 302' is advanced to a position proximate the tissue 308'. In the illustrated embodiment, the tissue stabilizer 304' comprises needles or barbs. Like the previous embodiments, the tissue stabilizer 304' may comprise vacuum attachment systems, balloon devices, and extendable wire tissue supports. The at least one tissue stabilizer 304' is deployed and the device is advanced such that the at least one tissue stabilizer engages the tissue 308'. Thereafter, the ablation member 310a, which includes an angular reflector 310b, is advanced into the tissue 308'. The angular reflector 310b permits the formation of transverse or angular holes, pockets, or channels within the tissue 308'. Exemplary angular reflectors 310b include, for example, mirrors, polished plates, prisms, and angular-cleaved fiber optics. Those skilled in the art will appreciate that the angular reflectors 310b of the present embodiment may be easily adapted for use with the ablating and injecting devices disclosed herein.

Figure 41A:
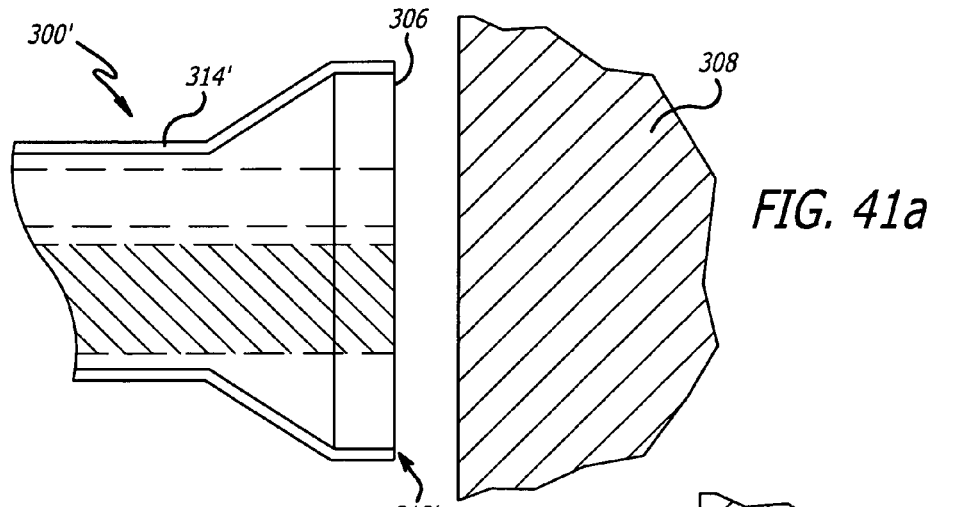
FIG. 41a is a schematic cross-sectional view yet another embodiment of a tissue-removal and medicament-delivery device of the present invention utilizing vacuum ports in communication with an external vacuum source to stabilize tissue.
Figure 41B:
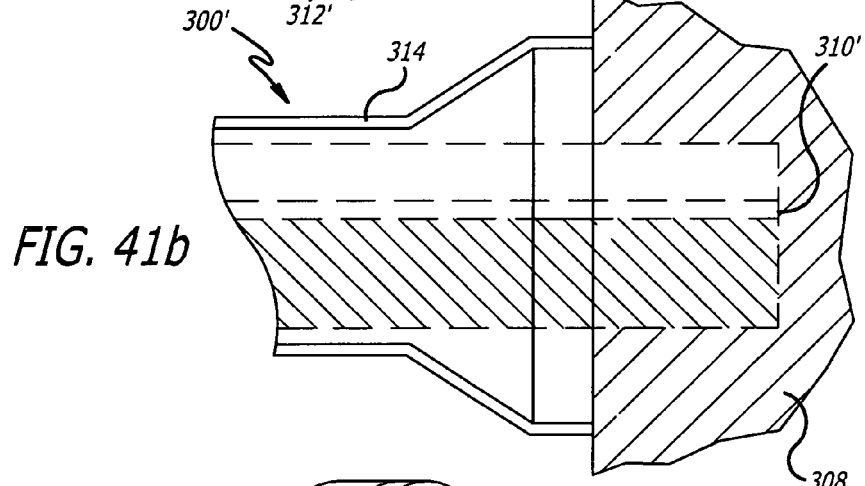
FIG. 41b is a schematic cross-sectional view of a step of an exemplary embodiment of a tissue-removal and medicament-delivery device of the present invention stabilizing tissue.
Figure 41C:
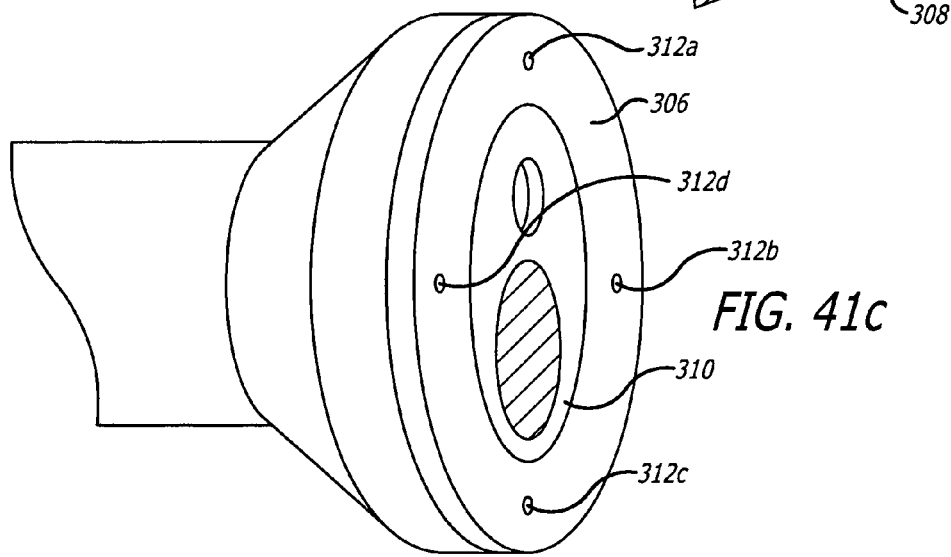
FIG. 41c is a perspective view of an exemplary embodiment of a tissue-removal and medicament-delivery device of the present invention having vacuum ports located on the device head.

In an alternate embodiment of the present invention, vacuum force may be used to anchor the device 300' to the tissue 308. As shown in FIG. 41a, the device 300' comprises at least one vacuum port 312' positioned radially about the tissue-engaging surface 306' and in communication at least one vacuum lumen 314' located within the device 300' to engage the tissue 308'. The device is advanced to a position proximal the tissue 308. An external vacuum source (not shown) is activated and a vacuum force is transmitted to the at least one vacuum port 312' through the vacuum lumen 314'. Thereafter, the device 300' is advance to engage the tissue 308, resulting in tissue 308 being retained by the device 300'. The ablating member 310' may then be advanced into the tissue 308. FIG. 41b shows the present invention retaining a portion of tissue 308' and advancing the ablating member 310' therein. FIG. 41c shows the distal portion of the present invention comprising a tissue ablating member 310 positioned thereon and having four vacuum ports 312a-d positioned on the tissue-engaging surface 306. Those skilled in the art will appreciate the present embodiment may be adapted for use with any of the embodiment disclosed within this present application.

Figure 42D:
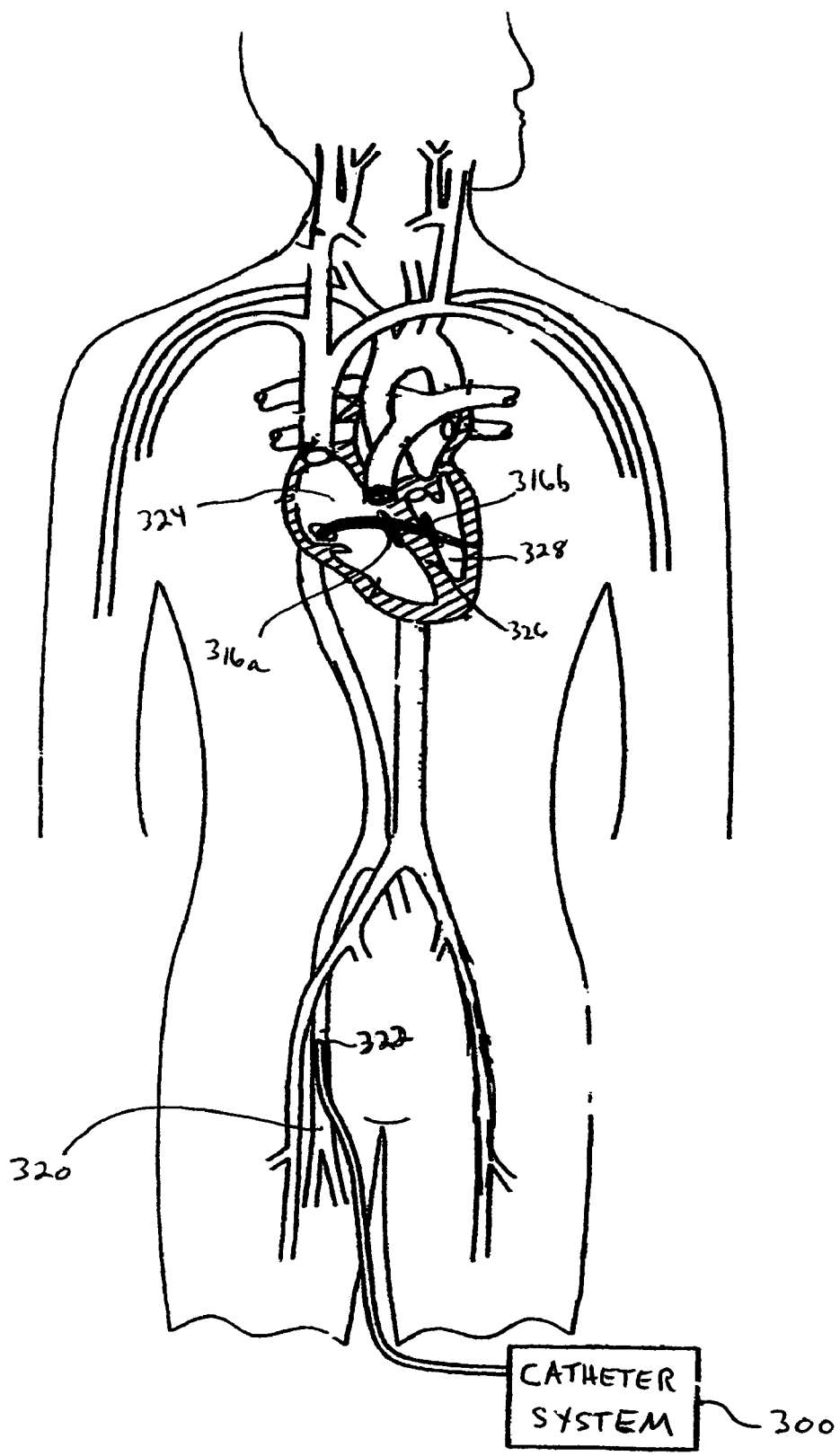
FIG. 42d is a front schematic view of patient's cardiovascular system illustrating the endoluminal introduction of a tissue-removal and medicament-delivery device of the present invention which is used to traverse the right atrium, puncture the atrial septum and enter the left atrium.

An alternate embodiment of the present invention is illustrated in FIG. 42a-42c. As shown in FIG. 42a, the device 300' comprises a deflated first balloon 316a and a deflated second balloon 316b in communication with at least one internal inflation lumen 318. The device 300' is advanced to a position proximate the area of interest and a hole 320 is formed in the tissue 308a. As shown in FIG. 42b, the distal portion of the device 300' and the deflated second balloon 316b is advanced therethrough. Thereafter, the first balloon 316a and the second balloon 316b are inflated, thereby supportively engaging the tissue 308a disposed therebetween. Thereafter the device 300' is advanced to and engages tissue 308b. Those skilled in the art will appreciate the present embodiment may be used to isolate discrete portion of tissue or organs. For example, as shown in FIG. 42d, the present invention may be utilized to sealably traverse the atrial septum 326 and precisely ablate and inject medicament to an isolated chamber 328 of the heart. FIG. 42c shows the distal portion of the present invention comprising a tissue ablating member 310 and having a first and second balloon 316a-b positioned thereon.

Figure 43A:
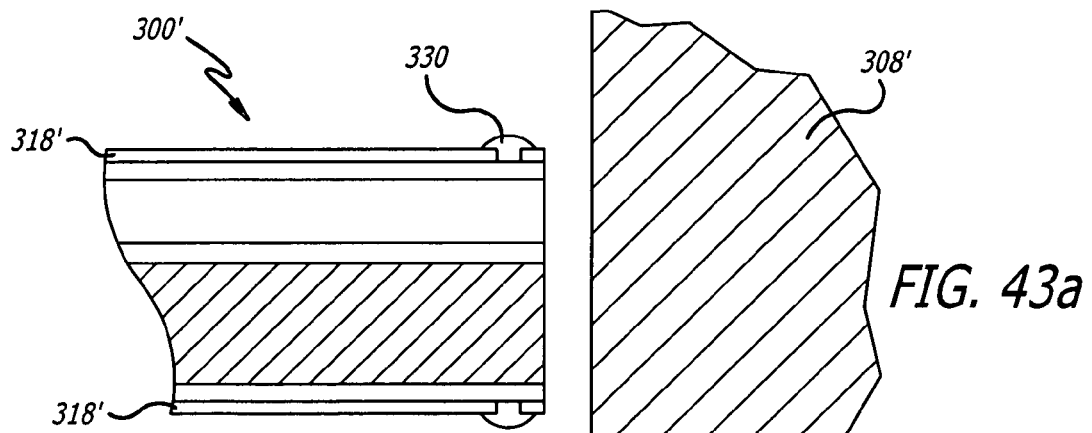
FIG. 43a is a schematic cross-sectional view yet another embodiment of a tissue-removal and medicament-delivery device of the present invention utilizing one balloons to stabilize and isolate tissue.
Figure 43B:
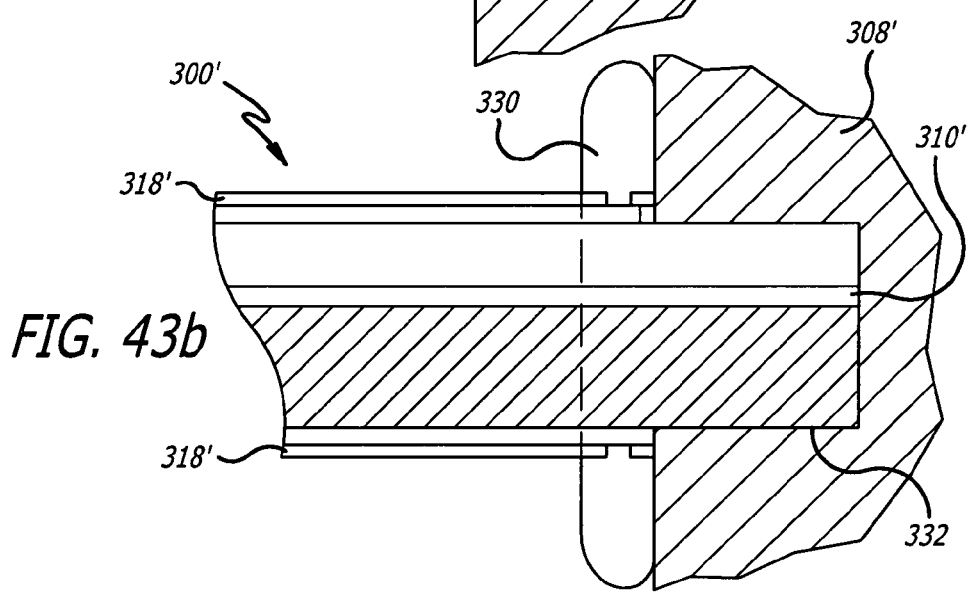
FIG. 43b is a schematic cross-sectional view of a step of an exemplary embodiment of a tissue-removal and medicament-delivery device of the present invention stabilizing and isolating tissue.
Figure 43C:
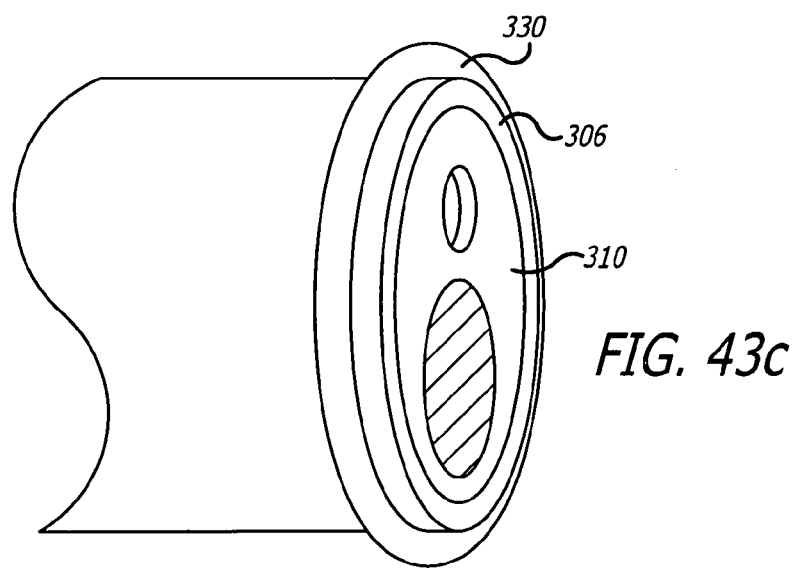
FIG. 43c is a perspective view of an exemplary embodiment of a tissue-removal and medicament-delivery device of the present invention having a balloon located proximate the device head.

As illustrated in FIG. 43a-43c, an alternate exemplary embodiment of the ablating and injecting device of the present invention is contemplated, wherein the distal portion of the device 300' further comprises at least one sealing balloon 330 in communication with at least one internal inflation lumen 318'. As shown in FIG. 43, the distal portion of device 300' is positioned proximate the tissue 308'. The at least one sealing balloon 330 is inflated and sealably engages the tissue 308'. Thereafter, a tissue channel 332 is formed by advancing the ablating member 334 into the tissue 308'. A medicament, for example an angiogenesis-inducing agent, may be applied through port 336 to the tissue 308' forming the channel 332. The at least one sealing balloon 330 prevents medicament washout by sealing the tissue channel 332. Those skilled in the art will appreciate that the sealable balloon 330 of the present embodiment may be used to stabilize a seal the device within a tissue lumen or channel.

FIG. 44a-44d show another embodiment of the present invention, comprising at least one user operable steering device 334 in communication with the flexible distal portion of the device 300'. The at least one steering mechanism 334 enables the flexible distal portion of the device 300' to be biased. Those skilled in the art of will appreciate the present embodiment permits catheter-based delivery of the ablation and injection system of the present invention. For example, as shown in FIG. 42d, the present device 300' may be introduced into the femoral vein of a patient 320 (or, alternatively the right jugular vein) through an endoluminal entry point 322 and advanced through the circulatory system eventually arriving at the heart. Upon arriving a the heart, the device 300' may be directed to traverse the right atrium 324 and puncture the atrial septum 326, thereby entering the left atrium 328, if desired. This method of access is known to physicians skilled in interventional cardiology. FIG. 44c-44d shows alternate embodiments of the present invention which utilize at least one user operable steering device 334' to bias the distal portion of the device 300'. The steering member 334' is positioned along the longitudinal axis of the device. To bias the distal portion of the device 300' the user urges the steering device 334' towards the distal portion of the device 300', thereby forcing the medial portion of the steering device 334' to advance through port 336 and biasing the flexible distal portion of the device 300'

In addition to removing or displacing tissue to form holes or channels by laser ablation or by high-frequency electrical energy, holes or channels may be formed in tissue mechanically with hot tips or biopsy needles, ultrasonically, or hydraulically with high-pressure water. The medicament can be growth factor, which may take many forms. For example, growth factor may be delivered as a protein solution. Alternatively, growth factor may be combined with a fibrin, collagen, or plasma to form a cellular matrix gel. Growth factor may also be mixed into a semi-solid using a biocompatible matrix. Further, growth factor may be delivered to tissue in an atomized form under pressure. The medicament can also be a gene that encodes for said growth factor, or any other therapeutic agent or gene therapy agent that promotes angiogenesis or any therapeutic agent for the treatment of cardiovascular disease. Whatever the form may be, the angiogenesis-promoting growth-factor solution is administered through the delivery lumen(s) to enhance and accelerate the angiogenic process. The growth factor solution may be driven into the channel and/or tissue using, for example, a pneumatic system, a mechanical system (e.g., a syringe-type system with a plunger), a hydraulic system (e.g., using fluids or gas), or a gravitational system.

Those skilled in the art will understand that the embodiments of the present invention described above exemplify the present invention and do not limit the scope of the invention to these specifically illustrated and described embodiments. The scope of the invention is determined by the terms of the appended claims and their legal equivalents, rather than by the described examples. In addition, the exemplary embodiments provide a foundation from which numerous alternatives and modifications may be made, which alternatives and modifications are also within the scope of the present invention as defined in the appended claims.

What is claimed is:

1. A method of delivering medicament to tissue while preventing medicament washout, comprising:
   providing a medicament delivery catheter having a tissue engaging surface with at least one vacuum operated tissue stabilizer port;
   providing access to a tissue surface;
   advancing the catheter to the tissue surface;
   positioning the tissue engaging surface proximate the tissue surface;
   sealably engaging the tissue engaging surface to the tissue surface by activating a vacuum force through the tissue stabilizer port;
   forming a sealed opening in the tissue surface;
   delivering medicament through the sealed opening in the tissue surface; and
   preventing the medicament from passing between the tissue engaging surface and the tissue surface to a location outside the sealed opening.

2. The method of claim 1 wherein the catheter comprises at least one vacuum port positioned radially about the tissue engaging surface and at least one vacuum lumen located within the catheter.

3. The method of claim 2 wherein the catheter comprises four vacuum ports positioned on the tissue engaging surface.

4. A method of delivering medicament to tissue while preventing medicament washout, comprising:
   providing a medicament delivery catheter having a tissue engaging surface with a sealing balloon;
   providing access to a tissue surface;
   advancing the catheter to the tissue surface;
   positioning the tissue engaging surface proximate the tissue surface;
   sealably engaging the tissue engaging surface to the tissue surface by inflating the sealing balloon;
   forming a sealed opening in the tissue surface;
   delivering medicament through the sealed opening in the tissue surface; and,
   preventing the medicament from passing between the tissue engaging surface and the tissue surface to a location outside of the sealed opening.

5. The method of claim 4 wherein forming a sealed opening in the tissue surface comprises maintaining the inflated balloon against the tissue surface while the opening is formed.

6. The method of claim 4 wherein the inflated balloon is maintained against the tissue opening while the medicament is delivered.

* * * * *